(12) United States Patent
Mumm et al.

(10) Patent No.: US 11,814,679 B2
(45) Date of Patent: Nov. 14, 2023

(54) INTERLEUKIN-10 PRODUCTION OF ANTIGEN-SPECIFIC CD8+ T CELLS AND METHODS OF USE OF SAME

(71) Applicant: Eli Lilly and Company, Indianapolis, IN (US)

(72) Inventors: John Brian Mumm, Los Altos Hills, CA (US); Ivan Ho Chan, Millbrae, CA (US); Scott McCauley, Brisbane, CA (US); Scott Ogg, San Francisco, CA (US); Martin Oft, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/061,591

(22) PCT Filed: Jan. 10, 2017

(86) PCT No.: PCT/US2017/012882
§ 371 (c)(1),
(2) Date: Jun. 12, 2018

(87) PCT Pub. No.: WO2017/123557
PCT Pub. Date: Jul. 20, 2017

(65) Prior Publication Data
US 2019/0032134 A1    Jan. 31, 2019

Related U.S. Application Data

(60) Provisional application No. 62/277,442, filed on Jan. 11, 2016.

(51) Int. Cl.
| | |
|---|---|
| *C12N 5/00* | (2006.01) |
| *A61K 39/00* | (2006.01) |
| *C12Q 1/6881* | (2018.01) |
| *A61K 38/20* | (2006.01) |
| *A61K 39/39* | (2006.01) |
| *A61K 47/60* | (2017.01) |
| *A61P 35/00* | (2006.01) |
| *A61K 35/17* | (2015.01) |
| *A61K 45/06* | (2006.01) |
| *C07K 14/725* | (2006.01) |
| *C12N 5/0783* | (2010.01) |

(52) U.S. Cl.
CPC ............ *C12Q 1/6881* (2013.01); *A61K 35/17* (2013.01); *A61K 38/2066* (2013.01); *A61K 39/0011* (2013.01); *A61K 39/39* (2013.01); *A61K 45/06* (2013.01); *A61K 47/60* (2017.08); *A61P 35/00* (2018.01); *C07K 14/7051* (2013.01); *C12N 5/0637* (2013.01); *A61K 2039/55527* (2013.01); *A61K 2039/572* (2013.01); *C12N 2501/998* (2013.01); *C12Q 2600/136* (2013.01)

(58) Field of Classification Search
None
See application file for complete search history.

(56) References Cited

U.S. PATENT DOCUMENTS

| | | |
|---|---|---|
| 7,052,686 B2 | 5/2006 | Lee et al. |
| 2014/0314795 A1 | 10/2014 | Riddell et al. |
| 2014/0349402 A1 | 11/2014 | Cooper et al. |

FOREIGN PATENT DOCUMENTS

| | | |
|---|---|---|
| WO | 200226265 | 4/2002 |
| WO | 2008054585 | 5/2008 |
| WO | 2010077853 | 7/2010 |
| WO | 2014172392 | 10/2014 |
| WO | 2015063176 A1 | 5/2015 |
| WO | 2015070060 | 5/2015 |
| WO | 2015108785 | 7/2015 |
| WO | 2015112626 | 7/2015 |
| WO | 2016064817 | 4/2016 |
| WO | 2016126615 | 8/2016 |
| WO | 2016191587 | 12/2016 |

OTHER PUBLICATIONS

Janeway et al., 2001, Immunobiology, 5th Ed., Garland Science, pp. 106-108, 117-118 and 260-263.*
Garcia et al., Cell, 2005, 122: 333-336.*
Manning et al., Immunity, 1998, 8:413-425.*
Kageyama et al (Clinical Cancer Research, 21(10):2268-2277, published on line Apr. 8, 2015.*
Robbins et al (Journal of Clinical Oncology 29(7):917-924, 2011).*
Robbins et al (Journal of Immunolgy, 180:6116-6131, 2008).*
Stone et al (Cancer Immunol Immunother, 63(11):1163-1176, Nov. 2014).*
He et al, Journal of Hematology & Oncology, 12:139, 2019.*
Abate-Daga et al (PLOS One 9(3):1-12, 2014).*
De Waal Malefyt, et al., "Interleukin 10(IL-10) Inhibits Cytokine Synthesis by Human Monocytes: An Autoregulatory Role of IL-10 Produced by Monocytes," *J. Exp. Med*, vol. 174, pp. 1209-1220 (1991).

(Continued)

*Primary Examiner* — Mark Halvorson
(74) *Attorney, Agent, or Firm* — Nielsen IP Law LLC

(57) ABSTRACT

The present disclosure provides methods and compositions relating to isolated CD8+ T cells expressing a disease antigen-specific T cell receptor, as well as nucleic acids encoding the Vα and Vβ polypeptide pairs of T cell receptors (TCRs) of such disease antigen-specific T cells. Such disease antigen-specific CD8+ T cells are obtainable from the periphery (e.g., blood) of a subject having a disease amenable to treatment with an IL-10 agent. The present disclosure also contemplates therapeutic methods and compositions relating to administration of isolated disease antigen-specific CD8+ T cells to a subject, as well as therapeutic methods and compositions relating to CD8+ T cells genetically modified to express a disease antigen-specific TCR and/or chimeric antigen receptor.

13 Claims, 8 Drawing Sheets

Specification includes a Sequence Listing.

(56) References Cited

OTHER PUBLICATIONS

De Waal Malefyt, et al., "Interleukin 10 (IL-10) and Viral IL-10 Strongly Reduce Antigen-specific Human T Cell Proliferation by Diminishing the Antigen-presenting Capacity of Monocytes via Downregulation of Class II Major Histocompatibility Complex Expression," *J. Exp. Med.*, vol. 174, pp. 915-924 (1991).

Emmerich, et al., "IL-10 Directly Activates and Expands Tumor-Resident CD8 T Cells without De Novo Infiltration from Secondary Lymphoid Organs," *Cancer Research*, vol. 72, No. 14, pp. 3570-3582 (2012).

Mumm, et al., "IL-10 Elicits IFNγ-Dependent Tumor Immune Surveillance," *Cancer Cell*, vol. 20, pp. 781-796 (2011).

Chan, et al., "The Potentiation of IFN-γ and Induction of Cytotoxic Proteins by Pegylated IL-10 in Human CD8 T Cells," *Journal of Interferon & Cytokine Research*, vol. 35, No. 12, pp. 948-955 (2015).

Infante, et al. "A first-in-human dose escalation study of PEGylated recombinant human IL-10 (AM0010) in advanced solid tumors," *Journal of Clinical Oncology*, 2015 ASCO Annual Meeting, vol. 33, No. 15 (2015).

Abate-Daga, D., et al. "Development of a T cell receptor targeting an HLA-A 0201 restricted epitope from the cancer-testis antigen SSX2 for adoptive immunotherapy of cancer." PloS one 9.3 (2014): e93321.

Emmerich, J. et al. "Autochthonous T cells to the rescue: IL-10 directly activates tumor-resident CD8+ T cells." Oncoimmunology 1.9 (2012): 1637-1639.

Gros, A., et al. "PD-1 identifies the patient-specific CD8+ tumor-reactive repertoire infiltrating human tumors." The Journal of clinical investigation 124 5 (2014): 2246-2259.

Infante, J. R., et al. "Abstract A194: PEGylated human IL-10 (AM0010) in advanced solid tumors." (2015): A194-A194.

Naing, A., et al. "PEGylated IL-10 (Pegilodecakin) induces systemic immune activation, CD8+ T cell invigoration and polyclonal T cell expansion in cancer patients." Cancer Cell 34.5 (2018): 775-791.

Rapoport, A. P., et al. "NY-ESO-1-specific TCR-engineered T cells mediate sustained antigen-specific antitumor effects in myeloma." Nature medicine 21.8 (2015): 914-921.

* cited by examiner

INTERLEUKIN-10 PRODUCTION OF ANTIGEN-SPECIFIC CD8+ T CELLS AND METHODS OF USE OF SAME

CROSS-REFERENCE TO RELATED APPLICATION

This application claims priority benefit of U.S. provisional application Ser. No. 62/277,442, filed Jan. 11, 2016, which application is incorporated herein by reference in its entirety.

FIELD OF THE INVENTION

This invention relates to methods of using IL-10 agents to elicit antigen-specific CD8+ T cells.

INTRODUCTION

The cytokine interleukin-10 (IL-10) is a pleiotropic cytokine that regulates multiple immune responses through actions on T cells, B cells, macrophages, and antigen presenting cells (APC). IL-10 can suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2- and IL-4-treated thymocytes, enhancing the viability of B cells, and stimulating the expression of MHC class II.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601).

IL-10 has classically been defined as an immune inhibitory cytokine (de Waal Malefyt et al. J Exp Med, 1991. 174(5): p. 1209-20; de Waal Malefyt et al., J Exp Med, 1991. 174(4): p. 915-24). Recent evidence clearly shows that the pegylated form of this cytokine exerts immunostimulatory effects in context of immuno-oncology (Emmerich et al. Cancer Res, 2012. 72(14): p. 3570-81; Mumm et al., Cancer Cell, 2011. 20(6): p. 781-96) The specific mechanism of this anti-tumor effect has been shown to require both CD8+ T cells and endogenous IFNγ (Mumm et al., supra). Specifically, CD8+ T cell exposure to IL-10/PEG-IL-10 leads to the potentiation of IFNγ, Granzyme B and Perforin secretion. The secretion of both IFNγ and Granzyme B are dependent upon T cell receptor engagement with cognate MHC I/antigen complexes (Chan et al, J Interferon Cytokine Res, 2015, 35(12): 948-955).

As a result of its pleiotropic activity, IL-10 has been linked to a broad range of diseases, disorders and conditions, including inflammatory conditions, immune-related disorders, fibrotic disorders, metabolic disorders and cancer. Clinical and pre-clinical evaluations with IL-10 for a number of such diseases, disorders and conditions have solidified its therapeutic potential.

Treatment of human cancer patients with PEG-rHuIL-10 (AM0010) monotherapy leads to substantial anti-tumor responses characterized by substantial increases in Granzyme B+ intratumoral CD8+ T cell infiltration. Concomitant with this activated CD8+ intratumoral T cell infiltrate are reproducible increases in the serum cytokines IFNγ, IL-18, IL-7, IL-4, GM-CSF and the activated T cell marker FasL (Infante, et al., ASCO Meeting Abstracts, 2015. 33(15_suppl): p. 3017). These cytokines are the hallmarks of broad spectrum immune activation.

SUMMARY

The present disclosure provides methods and compositions relating to isolated CD8+ T cells expressing a disease antigen-specific T cell receptor, as well as nucleic acids encoding the Vα and Vβ polypeptide pairs of T cell receptors (TCRs) of such disease antigen-specific T cells. Such disease antigen-specific CD8+ T cells are obtainable from the periphery (e.g., blood) of a subject having a disease amenable to treatment with an IL-10 agent. The present disclosure also contemplates therapeutic methods and compositions relating to administration of isolated disease antigen-specific CD8+ T cells to a subject, as well as therapeutic methods and compositions relating to CD8+ T cells genetically modified to express a disease antigen-specific TCR and/or chimeric antigen receptor.

Provided herein is a method of identifying a variable alpha (Vα) T cell receptor (TCR) polypeptide and/or a variable beta (Vβ) TCR polypeptide of a TCR of a disease antigen-specific T cell, the method including: administering an IL-10 agent to a subject having a disease amenable to IL-10 agent therapy; sequencing nucleic acids from a sample containing one or more CD8+ T cells obtained from the subject, wherein said sequencing comprises sequencing nucleic acids encoding a variable alpha (Vα) TCR polypeptide and/or nucleic acids encoding a variable beta (Vβ) TCR polypeptide; and comparing the abundance of the nucleic acids encoding the Vα TCR polypeptide and/or nucleic acids encoding the Vβ TCR polypeptide with the abundance of the nucleic acids encoding the Vα TCR polypeptide and/or nucleic acids encoding Vβ TCR polypeptide in a reference sample obtained from one or more patients having the disease amenable to IL-10 agent therapy either prior IL-10 agent therapy or at an earlier time point during IL10 agent therapy; wherein the Vα and/or Vβ TCR polypeptides which are present in the sample at greater abundance than in the reference sample represent a Vα/Vβ TCR polypeptide pair specific for a disease antigen-specific CD8+ T cell.

Also provided herein is a method of generating a vector encoding a variable alpha (Vα) T cell receptor (TCR) polypeptide and a variable beta (Vβ) TCR polypeptide of a TCR of a disease antigen-specific T cell, the method including: sequencing nucleic acids from a sample containing one or more CD8+ T cells obtained from a subject to whom IL-10 agent therapy has been administered for a disease amenable to IL-10 agent treatment, wherein the CD8+ T cells express a disease antigen-specific T cell receptor (TCR) comprising a variable alpha (Vα) TCR polypeptide and nucleic acid encoding a variable beta (Vβ) TCR polypeptide; and cloning nucleic acids encoding a Vα and Vβ TCR polypeptide pair of a TCR of a disease antigen-specific CD8+ T cell into one or more constructs to generate a vector encoding one or both of Vα and Vβ TCR polypeptides of a disease antigen-specific TCR, wherein Vα and/or Vβ TCR polypeptides which are present in the sample at greater abundance than in a reference sample obtained from one or more patients having the disease amenable to IL-10 agent therapy either prior IL-10 agent therapy or at an earlier time point during IL10 agent therapy represent the Vα/Vβ TCR polypeptide pair of a disease antigen-specific CD8+ T cell.

In any embodiment, the subject may exhibit at least stable disease or an at least partial response to IL-10 agent therapy. In some embodiments, the subject exhibits at least a partial response to IL-10 agent therapy.

In any embodiments, the sample may be enriched for PD1+, CD8+ T cells. In some embodiments, the PD1+, CD8+ T cells express cell surface PD1 at a level of at least PD1+ mid. In some embodiments, the PD1+, CD8+ T cells express cell surface PD1 at a level of at least PD1+ high.

In any embodiment, the sample may be enriched for CD45RO+, CD8+ T cells. In any embodiment, the sample may be enriched for IFNγ+, CD8+ T cells. In some embodiments, the sample is enriched for IFNγ+, CD45RO+, CD8+ T cells. In some embodiments, the sample is enriched for IFNγ+PD1+, CD8+ T cells. In some embodiments, the sample is enriched for PD1+, CD45RO+, CD8+ T cells. In some embodiments, the sample is enriched for IFNγ+ CD45RO+, PD1+, CD8+ T cells. In some embodiments, the method includes contacting the CD8+ T cells with a CD3 agonist to stimulate IFN☐☐expression. In some embodiments, the CD3 agonist is an anti-CD3 antibody.

In any embodiment, the sample may be derived from peripheral blood, lymph, or a tumor of the subject.

In any embodiment, the sample may be enriched for CD8+ T cells that are PD1+, IFNγ+, CD45RO+, Granzyme B+, and/or Perforin+.

In any embodiment, the one or more patients may include the subject. In some embodiments, the one or more patients is the subject.

In any embodiment, the method may include sequencing nucleic acid encoding the Vα TCR polypeptide and/or nucleic acid encoding the Vβ TCR polypeptide; determining the amino acid sequences of at least the complementarity determining regions (CDRs) the Vα TCR polypeptide and/or the Vβ TCR polypeptide; and comparing the abundance of the amino acid sequences of the Vα TCR polypeptide and/or amino acid sequences of the Vβ TCR polypeptide with the abundance of the amino acid sequences of the Vα TCR polypeptide and/or the amino acid sequences of the Vβ TCR polypeptide in a reference sample obtained from one or more patients having the disease amenable to IL-10 agent therapy either prior IL-10 agent therapy or at an earlier timepoint during IL10 agent therapy.

In any embodiment, the method may include assessing antigen specificity of a TCR expressed on a CD8+ T cell isolated according to an embodiment of a method of any one of identifying a variable alpha (Vα) T cell receptor (TCR) polypeptide and/or a variable beta (Vβ) TCR polypeptide of a TCR of a disease antigen-specific T cell, as described above, by comparing an amino acid sequence of the Vα and/or Vβ TCR polypeptides with amino acid sequences of Vα and/or Vβ TCR polypeptides in the reference sample.

Also provided herein is a method of obtaining amino acid sequences of a t cell receptor (TCR) of a disease antigen-specific T cell may include administering an interleukin (IL)-10 agent to a subject having a disease amenable to IL-10 agent therapy, wherein said administering is effective to provide for an at least partial response in the subject; obtaining peripheral blood lymphocytes (PBLs) from a subject having at least a partial response to the IL-10 agent therapy; isolating PD1+, CD8+ T cells from the PBLs; sequencing a nucleic acid encoding a variable alpha (Vα) TCR polypeptide and/or a nucleic acid encoding a variable beta (Vβ) TCR polypeptide, wherein the Vα TCR polypeptide and the beta TCR polypeptide are a Vα/Vβ TCR pair of a TCR expressed on a surface of the isolated PD1+, CD8+ T cells; and determining the amino acid sequences of the of Vα TCR polypeptide and/or the Vβ TCR polypeptide encoded by the sequenced nucleic acids, wherein the Vα and Vβ TCR polypeptides represent a Vα/Vβ TCR polypeptide pair specific for an antigen of the disease.

Also provided herein is a method of generating a vector encoding a variable alpha (Vα) T cell receptor (TCR) polypeptide and a variable beta (Vβ) TCR polypeptide of a TCR of a disease antigen-specific T cell, the method including: isolating PD1+, CD8+ T cells from peripheral blood lymphocytes (PBLs) from a subject exhibiting at least a partial response to the IL-10 agent therapy for a disease amenable to IL-10 agent treatment, and wherein the PD1+, CD8+ T cells express a disease antigen-specific TCR containing a Vα TCR polypeptide and a Vβ TCR polypeptide; and cloning nucleic acids encoding the Vα and Vβ TCR polypeptide pairs of a TCR of an isolated PD1+, CD8+ T cell into one or more constructs to generate a vector encoding one or both of Vα and Vβ TCR polypeptides of a disease antigen-specific TCR. In some embodiments, the vector is suitable for stable transfection of a CD8+ T cell facilitation expression of the Vα and Vβ TCR polypeptide pairs. In some embodiments, the Vα TCR polypeptide and the TCR polypeptide are cloned into the same vector. In some embodiments, the Vα TCR polypeptide and the Vβ TCR polypeptide are cloned into a vector so as to provide a nucleic acid encoding a full length alpha TCR polypeptide and encoding a full length beta TCR polypeptide. In some embodiments, the Vα TCR polypeptide and the Vβ TCR polypeptide are cloned into a vector so as to provide a nucleic acid encoding a single chain T cell receptor (scTv). In some embodiments, the scTv contains, from N-terminus to C-terminus, the Vβ TCR polypeptide, a linker, and the Vα TCR polypeptide. In some embodiments, the vector is an expression vector. In some embodiments, a plurality of nucleic acids encoding the Vα and Vβ TCR polypeptides of a plurality of Vα/Vβ TCR pairs of TCRs of the isolated PD1+, CD8+ T cells are cloned into a plurality of vectors to produce a library of constructs encoding Vα and Vβ TCR polypeptide pairs of the disease antigen-specific TCRs of the PD1+, CD8+ T cells. A library of nucleic acid vectors produced as described herein is also provided.

In any embodiment, the isolating may include isolating IFNγ+, CD45RO+, PD1+, CD8+ T cells. In some embodiments, the method includes contacting the PBLs or the isolated PD1+, CD8+ T cells with a CD3 agonist to stimulate IFNγ expression. In some embodiments, the CD3 agonist is an anti-CD3 antibody.

In any embodiment, the isolating may include isolating CD45RO+, PD1+, CD8+ T cells.

In any embodiment, the PD1+, CD8+ T cells may express cell surface PD1 at a level of at least PD1+ mid. In some embodiments, the PD1+, CD8+ T cells express cell surface PD1 at a level of at least PD1+ high.

In any embodiment, the PD1+, CD8+ T cells may express one or more of IFNγ, CD45RO, Granzyme B, and Perforin.

In any embodiment, the subject may have a tumor, and the PD1+, CD8+ T cells may be specific for a tumor antigen. In some embodiments, the PD1+, CD8+ T cells may be tumor infiltrating lymphocytes. In some embodiments, the tumor is a solid tumor. In some embodiments, the tumor is a tumor of a cancer selected from cancer of the uterus, cervix, breast, prostate, testes, gastrointestinal tract, kidney, renal cell, bladder, bone, bone marrow, skin, head or neck, liver, gall bladder, heart, lung, pancreas, salivary gland, adrenal gland, thyroid, brain, ganglia, central nervous system (CNS) and peripheral nervous system (PNS), or cancer of the hematopoietic system, spleen, or thymus. In some embodiments, the tumor is a tumor of a cancer of the esophagus, oropharynx, stomach, small intestine, large intestine, colon, or rectum. In some embodiments, the tumor is a melanoma, colorectal cancer, or renal cancer.

In any embodiment, the subject may have a viral infection, and the PD1+, CD8+ T cells may be specific for an antigen of the infecting virus. In some embodiments, the virus is a hepadnavirus, flavivirus, retrovirus, herpes virus. In some embodiments, the virus is hepatitis B virus, hepatitis C virus, cytomegalovirus (CMV) or human immunodeficiency virus (HIV).

In any embodiment, the IL-10 agent may be human IL-10.

In any embodiment, the IL-10 agent may be a pegylated IL-10 (PEG-IL-10). In some embodiments, the PEG-IL-10 includes at least one PEG molecule covalently attached to an N-terminal amino acid residue of at least one monomer of IL-10. In some embodiments, the PEG-IL-10 includes a mixture of mono-pegylated IL-10 and di-pegylated IL-10. In some embodiments, the PEG component of the PEG-IL-10 has a molecular mass from 5 kDa to 30 kDa.

In any embodiment, the IL-10 agent may be administered subcutaneously to the subject.

In any embodiment, the subject may be a human subject.

In any embodiment, the method may include: sequencing nucleic acids encoding the Vα TCR polypeptide and/or nucleic acids encoding the Vβ TCR polypeptide; determining the amino acid sequences of the Vα TCR polypeptide and/or the Vβ TCR polypeptide; and analyzing the amino acid sequences of the Vα TCR polypeptide and/or the Vβ TCR polypeptide to identify the complementarity determining regions (CDRs) of the Vα TCR polypeptide and/or the Vβ TCR polypeptide.

In any embodiment, the method may include: assessing antigen specificity of a TCR expressed on the isolated PD1+, CD8+ T cells by comparing the amino acid sequences of the Vα and/or Vβ TCR polypeptides with the amino acid sequence of Vα and/or Vβ TCR polypeptides of a TCR expressed on T cells present in diseased tissue prior to administering the IL-10 agent.

Also provided herein is a method of generating a genetically modified T cell, the method including introducing into a CD8+ T cell a construct obtained by any embodiment of a method of generating a vector encoding a variable alpha (Vα) T cell receptor (TCR) polypeptide and a variable beta (Vβ) TCR polypeptide of a TCR of a disease antigen-specific T cell, as described above, to produce a genetically modified T cell expressing the Vα and Vβ TCR polypeptide pair of a disease antigen-specific TCR. In some embodiments, the Vα TCR polypeptide and the Vβ TCR polypeptide are encoded from separate expression cassettes on the same or different expression constructs. In some embodiments, the Vα TCR polypeptide encoded by the construct is operably linked at its C-terminus to a constant alpha TCR polypeptide. In some embodiments, the Vβ TCR polypeptide encoded by the construct is operably linked at its C-terminus to a beta constant TCR polypeptide. In some embodiments, the construct includes a nucleic acid encoding a single chain TCR (scTv) containing the Vβ TCR polypeptide and the Vα TCR polypeptide. In some embodiments, the scTv includes, from N-terminus to C-terminus, the Vβ TCR polypeptide, a linker, and the Vα TCR polypeptide. A population of genetically modified CD8+ T cells produced by a method as described herein is also provided.

Also provided herein is a method of treating a subject having a disease amenable to CD8+ T cell therapy, the method including: administering to the subject a genetically modified CD8+ T cell, wherein the T cell is genetically modified to express a recombinant TCR containing a Vα TCR polypeptide and a Vβ TCR polypeptide of a Vα/Vβ pair of a disease antigen-specific TCR specific for an antigen of the disease of the subject; wherein said administering is effective to treat the disease in the subject. In some embodiments, the amino acid sequences of the CDRs of the Vα TCR polypeptide and of the CDRs of the Vβ TCR polypeptide were identified according to any embodiment of a method of obtaining amino acid sequences of a T cell receptor (TCR) of a disease antigen-specific T cell, as described above. In some embodiments, the amino acid sequences of the Vα TCR polypeptide and of the Vβ TCR polypeptide were identified according to a method including sequencing nucleic acids encoding the Vα TCR polypeptide and/or nucleic acids encoding the Vβ TCR polypeptide; determining the amino acid sequences of the Vα TCR polypeptide and/or the Vβ TCR polypeptide; and analyzing the amino acid sequences of the Vα TCR polypeptide and/or the Vβ TCR polypeptide to identify the complementarity determining regions (CDRs) of the Vα TCR polypeptide and/or the Vβ TCR polypeptide.

In any embodiment, the Vα TCR polypeptide and the Vβ TCR polypeptide of the genetically modified T cell may be encoded from separate expression cassettes of the same or different expression constructs. In some embodiments, the Vα TCR polypeptide of the genetically modified T cell is encoded by the construct is operably linked at its C-terminus to a constant alpha TCR polypeptide. In some embodiments, the Vβ TCR polypeptide of the genetically modified T cell is encoded by the construct is operably linked at its C-terminus to a beta constant TCR polypeptide. In some embodiments, the Vβ TCR polypeptide and the Vα TCR polypeptide of the genetically modified T cell are encoded by a construct containing a nucleic acid encoding a single chain TCR (scTv) containing the Vβ TCR polypeptide and the Vα TCR polypeptide. In some embodiments, the scTv contains, from N-terminus to C-terminus, the Vβ TCR polypeptide, a linker, and the Vα TCR polypeptide.

In any embodiment, the disease amenable to CD8+ T cell therapy may be cancer and the disease antigen-specific TCR of the genetically modified CD8+ T cell may be specific for an antigen of the cancer. In some embodiments, the cancer is a solid tumor. In some embodiments, the tumor is a tumor of a cancer selected from cancer of the uterus, cervix, breast, prostate, testes, gastrointestinal tract, kidney, renal cell, bladder, bone, bone marrow, skin, head or neck, liver, gall bladder, heart, lung, pancreas, salivary gland, adrenal gland, thyroid, brain, ganglia, central nervous system (CNS) and peripheral nervous system (PNS), or cancer of the hematopoietic system, spleen, or thymus. In some embodiments, the cancer is a cancer of the esophagus, oropharynx, stomach, small intestine, large intestine, colon, or rectum. In some embodiments, the cancer is melanoma, colorectal cancer, or renal cancer.

In any embodiment, the disease amenable to CD8+ T cell therapy may be a viral infection, and the disease antigen-specific TCR of the genetically modified CD8+ T cell may be specific for an antigen of the virus. In some embodiments, the virus is a hepadnavirus, flavivirus, retrovirus, herpes virus. In some embodiments, the virus is hepatitis B virus, hepatitis C virus, cytomegalovirus (CMV) or human immunodeficiency virus (HIV).

In any embodiment, the method may include administering a further therapeutic agent. In some embodiments, the therapeutic agent is an IL-10 agent. In some embodiments, the disease amenable to CD8+ T cell therapy is a cancer and the therapeutic agent is a chemotherapeutic agent. In some embodiments, the disease amenable to CD8+ T cell therapy is a viral infection and the therapeutic agent is an antiviral agent In any embodiment, the administering may include administering a plurality of genetically modified CD8+ T cells, wherein the genetically modified CD8+ T cells of the plurality include genetically modified CD8+ T cells containing different disease antigen-specific TCRs. In some embodiments, the genetically modified CD8+ T cells are autologous to the subject.

Other embodiments will be apparent to the skilled artisan based on the teachings of the present disclosure.

DETAILED DESCRIPTION

Figure 1:
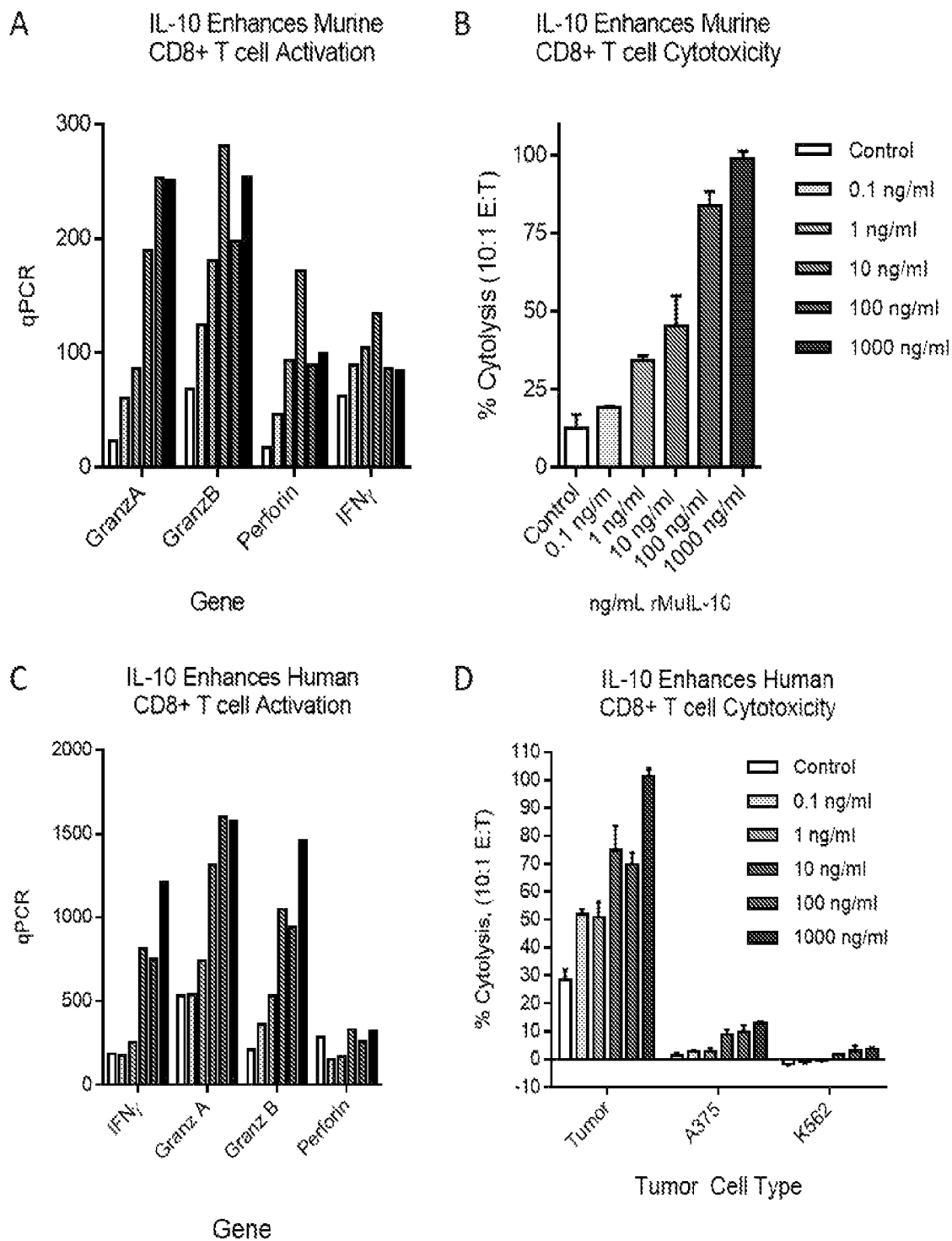
FIG. 1 (Panels A-D) illustrates the effects of IL-10 on murine CD8+ T cell function (Panels A-B) and human CD8+ T cell function (Panels C-D) as tested in vitro.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

Therapy with genetically modified CD8+ T cells, such as CAR-T T cell therapy, is a therapeutic approach for the treatment of, for example, cancer-related (e.g., B and T cell lymphomas) and immune-related malignancies. CAR-T T cells generally comprise patient-derived memory CD8+ T cells genetically modified to express a recombinant T cell receptor specific for a known antigen present on, for example, a tumor of interest. While the present disclosure is generally described in the context of using CAR-T cell therapy for the treatment of cancer, it is to be understood that such therapy also finds utility in the treatment of other indications, such as viral infections (e.g., HBV, HCV, HIV, CMV).

One challenge in development of CAR-T T cell therapies is the identification of suitable variable alpha (Vα) and variable beta (Vβ) TCR polypeptides of a Vα/Vβ TCR pair for use in CAR-T polypeptides so as to provide for a desired antigen specificity of the TCR of the genetically modified CD8+ T cell.

As described herein, the treatment of cancer patients with PEG-IL-10 leads to the accumulation in peripheral blood of tumor antigen-specific, PD1+CD8+ T cells. This phenomenon is concomitant with an increase of Granzyme B+, CD8+ tumor infiltrating lymphocytes, (TILs). Treatment of cancer patients with PEG-IL-10 leads to the accumulation of cytotoxic, tumor antigen specific CD8+ T cells. Of this population, PD1+ mid to PD1+ high peripheral CD8+ T cells represent unique alpha beta TCR sequences that recognize tumor associated and specific antigens. These cells isolated from cancer patients in response to treatment with PEG-IL-10 provide high affinity, maturation selected, TCR sequences to tumors (e.g., solid tumors) that are not achievable via modeling from murine tumor models. Investigation of the sequences generated by treatment with PEG-IL-10 (either as a monotherapy or in combination with immune checkpoint therapy and/or chemotherapy) in the same tumor indication and same MHC haplotype will provide for Vα/Vβ TCR pairs that are specific for currently unknown tumor antigens, and that can be capable of eliciting a productive anti-tumor immune response.

The present disclosure provides methods of generating and isolating disease antigen-specific CD8+ T cells from patients following treatment with an IL-10 agent, as well as identification of the amino acid sequences of the variable alpha (Vα) and variable beta (Vβ) TCR polypeptides, and/or CDRs of the variable alpha (Vα) and variable beta (Vβ) TCR polypeptides, of the Vα/Vβ TCR pair of TCRs of such disease antigen-specific CD8+ T cells. In some embodiments, the antigen-specific CD8+ T cells are peripheral CD8+ T cells that are also PD1+. The encoding nucleic acids and/or information obtained therefrom can be used to produce individual constructs and/or a library of constructs encoding such Vα/Vβ TCR pairs. Such nucleic acids, and/or information obtained therefrom, can be used to produce genetically modified CD8+ T cells expressing a recombinant TCR comprising such a Vα/Vβ TCR polypeptide pair (or at least CDRs of such Vα/Vβ TCR polypeptides), where the recombinant TCR can be a CAR-T comprising a single chain T cell receptor (scTv) comprising a Vβ polypeptide operably linked to a Vα polypeptide, e.g., through a linker. The present disclosure further contemplates methods of treating cancer patients and or patients with diseases that are amenable to CD8+ T cell therapy, such as chronically virally infected patients (e.g., HBV infected patients).

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based upon a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration can be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The present disclosure in some embodiments involves analysis of expression of markers, e.g., cell surface markers, using flow cytometry. A cell can be classified as "positive" or "negative" based on the relative intensity of detectable label (e.g., fluorescence) following staining with a marker-specific reagent (e.g., fluorescently-labeled antibody) as assessed by flow cytometry. Generally, the cells are distinguished according to their expression levels based upon readily discernible differences in staining of a bimodally distributed marker, e.g., CD8, PD1, IFNγ, CD45RO, Granzyme B, Perforin and the like. In some embodiments, the frequency distribution of the marker staining is obtained for all the cells and the population curve fit to a higher staining and lower staining population, and cells assigned to the population to which they most statistically are likely to belong in view of a statistical analysis of the respective population distributions. In some embodiments, the frequency distribution of the marker staining is obtained for all the cells and the population curve fit to a higher staining, mid-level staining, and lower staining populations, and cells assigned to a "high", "mid", and or "low" population to which they most statistically are likely to belong in view of a statistical analysis of the respective population distributions. Methods of segregating T cells into + and − categories, as well as into "high", "mid", and or "low" categories, are known to persons of ordinary skill in the art.

Thus, for example, the present disclosure contemplates analysis of PD1 expression on T cells. T cells exhibit a substantially bimodal distribution of PD1 (also known as CD279) cell surface expression, where cells around the higher peak of PD1 cell surface expression may be classified as "PD1high" (or "PD1+") and cells around the lower peak of PD1 cell surface expression may be classified as "PD1low" (or "PD1-"). The population of CD8+ T cells that include activated CD8+ T cells may also include an intermediate population of cells ("PD1mid") in between PD1high and PD1low cells, where PD1mid cells have a level of PD1 cell surface expression that is higher than PD1 low cells, but lower than PD1 high cells. Thus, activated CD8+ T cells of interest may include an intermediate ("mid")-to-high level of cell surface expression of PD1 ("PD1mid-high"). In other words, the activated CD8+ T cells may be a population of CD8+ T cells that do not have a low expression of PD1 on the cell surface (i.e., that are not "PD1low").

As used herein "PD1mid" refers to a level of cell surface expression of PD1 which is about at least 100-150 times the lowest level of PD1 expression in the cell population ("PD1low"), and less than about ⅓ of the highest level of PD1 expression in the cell population ("PD1high"), where cell surface PD1 expression is detected by flow cytometry. For example, "PD1 mid" cells may express a level of cell surface PD1 that results in a mean channel fluorescent detection by flow cytometry of approximately 3000, while low PD1 expression ("PD1low") is represented by a mean channel fluorescence detection of approximately 200 and "PD1high" expression is represented by a mean channel fluorescence detection of approximately 9000. It should be noted that "PD1low" cells, when characterizing cells as either PD1+ or PD1, "PD1low" are considered PD1 negative ("PD1-").

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule can be more permeable to cells, less susceptible to degradation, and less likely to elicit an immune response than large molecules.

The term "ligand" refers to a molecule, or complex thereof, that can act as an agonist or antagonist of a receptor. The term "ligand" encompasses natural and synthetic ligands, e.g., cytokines, cytokine variants, analogs, muteins, and binding compositions derived from antibodies. The term "ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. The term "ligand" also includes a membrane-bound ligand that has been changed, e.g., by chemical or recombinant methods, to a soluble version of the membrane-bound ligand. A receptor can be intracellular, that is, it can reside in the cytosol, nucleus, or some other intracellular compartment or be associated with, and potentially transverse the cell membrane, yet possess a ligand binding site on the intracellular surface of the cell membrane. The complex of a ligand and receptor is termed a "ligand-receptor complex."

The terms "inhibitors" and "antagonists", or "activators" and "agonists", refer to inhibitory or activating molecules, respectively, e.g., a ligand, receptor, cofactor, gene, cell, tissue, or organ. Inhibitors are molecules that decrease, block, prevent, delay activation, inactivate, desensitize, or down-regulate the activity of a biological molecule, e.g., a gene, protein, ligand, receptor, or cell. Activators are molecules that increase, activate, facilitate, enhance activation, sensitize, or up-regulate the activity of a biological molecule, e.g., a gene, protein, ligand, receptor, or cell. An inhibitor can also be defined as a molecule that reduces, blocks, or inactivates a constitutive activity. An "agonist" is a molecule that interacts with a target to cause or promote an increase in the activity of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule, either alone or in combination with other factor, to regulate, increase or decrease the function or activity of another biological molecule, either directly or indirectly. The term "modulator" is meant to refer broadly to molecules that can regulate the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator can act alone, or it can use a cofactor, e.g., a protein, metal ion, or small molecule.

The "activity" of a molecule can describe or refer to, for example: (a) the binding of the molecule to a ligand or to a receptor; (b) the level of response of a ligand when bound to its receptor, to catalytic activity; (c) the ability to stimulate gene expression or cell signaling, differentiation, or maturation; (d) antigenic activity; and/or (e) the modulation of activities of other molecules. The term can also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, cell division.

As used herein, "comparable", "comparable activity", "activity comparable to", "comparable effect", "effect comparable to", "similar" and "substantially similar" are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect can refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length. Polypeptides may include genetically coded and non-genetically coded amino acids, chemically modified amino acids, and polypeptides having modified polypeptide backbones. Examples of polypeptides include, but are not limited to, fusion proteins including fusion proteins with a heterologous amino acid sequence; fusion proteins with heterologous and homologous leader sequences; fusion proteins with or without N-terminal methionine residues; fusion proteins with immunologically tagged proteins; and the like.

It will be appreciated that throughout this disclosure reference is made to genetically coded L-amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). The term "mutein" refers to proteins that are modified by single or multiple amino acid substitutions. Muteins are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

As used with respect to polypeptides and nucleic acids, the term "derived from", refers to a polypeptide or nucleic acid comprising an amino acid or nucleotide sequence that is derived from a reference polypeptide or nucleic acid (e.g., a naturally occurring polypeptide or nucleic acid), and is not limited to the source of the reference molecule nor the method by which the reference molecule was modified. By way of example, the term "derived from" includes homologs or variants of reference amino acid or DNA sequences.

In the context of a polypeptide or nucleic acid, the term "isolated" refers to a polypeptide or nucleic acid of interest that, if naturally occurring, is in an environment different from that in which it can naturally occur. "Isolated" is meant to include polypeptides or nucleic acid that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a molecule of interest is present in a) a greater concentration (e.g., at least 3-fold greater, at least 4-fold greater, at least 8-fold greater, at least 64-fold greater, or more) than the concentration of the molecule of interest in the starting sample. The starting sample may be a biological sample (e.g., a sample in which the molecule of interest naturally occurs or in which the molecule of interest is present after administration), or from a source where the concentration of the molecule of interest is greater than the environment (e.g. from a recombinant bacterial cell in which a polypeptide was expressed).

The term "substantially pure" refers to a composition containing a component of interest wherein the component of interest (e.g., a polypeptide) makes up greater than about 50% of the total content of the composition, and typically greater than about 60% of the total content of the composition. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

As used herein, the terms "specifically binds" or "selectively binds", refers to the interaction of a ligand with its receptor, antibody with its antigen, or other binding pair. The selective binding may be used to indicate the presence of the ligand in a heterogeneous mixture. Thus, under designated conditions, a ligand is deemed to selectively bind to its receptor where it binds to that receptor and does not bind to a substantial degree to other components of a heterogenous mixture. With respect to immunoglobulins, an immunoglobulin that selectively binds to an antigen binds with an affinity to its antigen, or a variant or mutein thereof, with an affinity that is at least two-fold greater, at least ten times greater, at least 20-times greater, or at least 100-times greater than the affinity than any other antigen. In a particular embodiment, the immunoglobulin that specifically binds to an antigen will have an affinity that is greater than about $10^9$ liters/mol, as determined by, e.g., Scatchard analysis (Munsen, et al. 1980 Analyt. Biochem. 107:220-239).

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it can correspond to a sequence of a naturally occurring human polypeptide or nucleic acid molecule including naturally occurring isoforms.

"Expressed on" as used herein, may be used to describe a cellular moiety (e.g., proteins or complexes thereof), that is present on the surface of a cell, usually as a result of production of the cellular moiety, or a precursor thereof, in the cell and translocation of the cellular moiety, or a precursor thereof, to the extracellular surface of the plasma membrane of the cell.

"Programmed cell death protein 1" or "PD1" refers to a cell surface receptor belonging to the immunoglobulin superfamily expressed on a subset of lymphocytes, and is also known as CD279. Human PD1 (Gene ID: 5133) is encoded by the PDCD1 gene.

"CD45RO" refers to an isoform of CD45, a receptor type protein tyrosine phosphatase family member, expressed on a subset of lymphocytes. Other isoforms of CD45 include CD45RA, CD45RB, CD45RC, CD45RAB, CD45RAC, CD45RBC, and CD45R (ABC). CD45RO is an isoform of CD45 that is shorter than the other isoforms and lacks CD45 exons known as RA, RB and RC. Human CD45 (Gene ID: 5788) is encoded by the PRPRC gene.

"Antigen-specific T cell" and "T cell that is specific to an antigen" as used herein, refer to a T cell expressing on its cell surface a T cell receptor (TCR) that specifically binds to an antigen by virtue of the structure of TCR polypeptides, such as the α and β polypeptide chains, containing variable regions. T cells whose TCR is specific to an antigen may have undergone recombination of the TCR genomic locus during maturation, and/or may have been genetically modified to express one or more TCR polypeptides or engineered TCR-like receptors (such as chimeric antigen receptors).

A "disease antigen" or "disease-associated antigen" refers to an epitope (e.g., an antigenic peptide, lipid, polysaccharide, nucleic acid, etc.) that elicits an immune response, such as a T-cell mediated immune response. Where the disease is a tumor, a tumor antigen or tumor-associated antigen may be an epitope expressed on a tumor cell. The tumor antigen may be unique to a tumor cell and not normally expressed on other cells of the body, particularly of the same lineage. In some cases, the tumor antigen may be an epitope normally expressed in other cells of the body, but does not induce an immune response in a non-tumor context. A tumor antigen may possess one or more epitopes that are typically expressed on normal cells during fetal development when the immune system is immature and unable to respond. A tumor antibody may possess one or more epitopes that are normally present at extremely low levels on normal cells but which are expressed at significantly higher levels on tumor cells, Overview of Method of Producing Disease Antigen Specific CD8+ T Cells The present disclosure provides, in one embodiment, a method of inducing expansion of disease antigen-specific CD8+ T cells into the periphery of a patient having a disease treatable with an IL-10 agent therapy, the method comprising the administration of an IL-10 agent to the patient in an amount effective to elicit induction of such disease antigen-specific CD8+ T cells, obtaining disease antigen-specific CD8+ T cells from a patient (e.g., CD8+ T cells in a tissue sample, such as a peripheral blood sample, of a patient). Accordingly, the present disclosure provides IL-10 agents, methods of production of IL-10 agents, dosing regimen for production of disease antigen-specific CD8+ T cells and for IL-10 agent therapy, methods for producing disease antigen-specific CD8+ T cells, analysis of TCRs of such T cells, production of libraries of TCR alpha and beta sequences and nucleic acids, analysis of antigen specificity of TCRs of such T cells, production of genetically modified T cells expressing a recombinant TCR (e.g., a CAR-T) comprising TCR alpha and beta sequences of disease antigen-specific TCRs of such T cells, genetically modified T cell compositions as well as their methods of production and use in therapy, and pharmaceutical compositions and kits. In some embodiments, the antigen-specific CD8+ T cells are peripheral CD8+ T cells that are also PD1+. These features of the present disclosure are described below.

IL-10 Agents (e.g., PEG-IL-10)

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-γ, IL-2, IL-3, TNFα and GM-CSF, IL-10 is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds. The IL-10 dimer becomes biologically inactive upon disruption of the non-covalent interactions between the two monomer subunits.

The present disclosure contemplates human IL-10 (NP_000563) and murine IL-10 (NP_034678), which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

The terms "IL-10", "IL-10 polypeptide(s), "IL-10 molecule(s)", "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists.

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

The utility of recombinant human IL-10 is frequently limited by its relatively short serum half-life, which can be due to, for example, renal clearance, proteolytic degradation and monomerization in the blood stream. As a result, various approaches have been explored to improve the pharmacokinetic profile of IL-10 without disrupting its dimeric structure and thus adversely affecting its activity. Pegylation of IL-10 results in improvement of certain pharmacokinetic parameters (e.g., serum half-life) and/or enhancement of activity.

As used herein, the terms "pegylated IL-10" and "PEG-IL-10" refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. As used herein, the terms "dipegylated IL-10" and "di-PEG-IL-10" indicate that at least one polyethylene glycol molecule is attached to a single residue on each subunit of the IL-10 dimer, generally via a linker.

In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein.

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity. The biological activity of PEG-IL-10 is typically measured by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686.

IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some can be post-translational variants, e.g., glycosylated variants. Any variant of IL-10 can be used provided it retains a suitable level of IL-10 activity.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions can be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides can be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides can be isolated from a natural source (e.g., an environment other than its naturally-occurring environment) and can also be recombinantly made (e.g., in a genetically modified host cell such as bacteria, yeast, Pichia, insect cells, and the like), where the genetically modified host cell is modified with a nucleic acid comprising a nucleotide sequence encoding the polypeptide. The IL-10 polypeptides can also be synthetically produced (e.g., by cell-free chemical synthesis).

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

Methods of Production of IL-10

A polypeptide of the present disclosure can be produced by any suitable method, including non-recombinant (e.g., chemical synthesis) and recombinant methods.

Chemical Synthesis

Where a polypeptide is chemically synthesized, the synthesis can proceed via liquid-phase or solid-phase. Solid-phase peptide synthesis (SPPS) allows the incorporation of unnatural amino acids and/or peptide/protein backbone modification. Various forms of SPPS, such as 9-fluorenylmethoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis can be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α, α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6- -trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethyl sulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained can be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide can be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that can be used as host cells include insect cells, mammalian cells, and/or plant cells. Where mammalian host cells are used, they can include human cells (e.g., HeLa, 293, H9 and Jurkat cells); mouse cells (e.g., NIH3T3, L cells, and C127 cells); primate cells (e.g., Cos 1, Cos 7 and CV1); and hamster cells (e.g., Chinese hamster ovary (CHO) cells).

A variety of host-vector systems suitable for the expression of a polypeptide can be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and can provide for inducible or constitutive expression where the coding region is operably-linked under the transcriptional control of the transcriptional initiation region, and a transcriptional and translational termination region. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host can be present to facilitate selection of cells containing the vector. Moreover, the expression construct can include additional elements. For example, the expression vector can have one or two replication systems, thus allowing it to be maintained in organisms, for example, in mammalian or insect cells for expression and in a prokaryotic host for cloning and amplification. In addition, the expression construct can contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein can be isolated using metal chelate chromatography methods. Proteins can contain modifications to facilitate isolation.

The polypeptides can be prepared in substantially pure or isolated form (e.g., free from other polypeptides). The polypeptides can be present in a composition that is enriched for the polypeptide relative to other components that can be present (e.g., other polypeptides or other host cell components). For example, purified polypeptide can be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide can be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —$CH_2NH$—, —$CH_2S$—, —$CH_2CH_2$—, —CH=CH-(cis and trans), —$COCH_2$—, —CH(OH)$CH_2$— or —$CH_2SO$—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C1-C10 carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —$(CH2)_n$—CO— or —$(CH2)_n$—$C_6H_4$—CO—) with functional groups which allow for the introduction of a bridge. Some examples are disulfides, disulfide mimetics such as the —$(CH2)_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO: 1); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO: 2); Transportan GWTLNSAGYLLGKINLKALAALAKKIL (SEQ ID NO: 3); KALAWEAKLAKALAKALAKHLAKALAKALKCEA (SEQ ID NO: 4); and RQIKIWFQNRRMKWKK (SEQ ID NO: 5). Exemplary PTDs include, but are not limited to, YGRKKRRQRRR (SEQ ID NO:6), RKKRRQRRR (SEQ ID NO:7); an arginine homopolymer of from 3 arginine residues to 50 arginine residues; exemplary PTD domain amino acid sequences include, but are not limited to, any of the following: YGRKKRRQRRR (SEQ ID NO: 8); RKKRRQRR (SEQ ID NO:9); YARAAARQARA (SEQ ID NO: 10); THRLPRRRRRR (SEQ ID NO: 11); and GGRRARRRRRR (SEQ ID NO: 12).

The carboxyl group $COR_3$ of the amino acid at the C-terminal end of an IL-10 polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched C1-C6-alkyl alcohols, e.g., ethyl alcohol or tert-butanol. The carboxyl group can also be amidated with primary or secondary amines such as ammonia, branched or unbranched C1-C6-alkylamines or C1-C6 di-alkylamines, e.g., methylamine or dimethylamine.

The amino group of the amino acid NR1R2 at the N-terminus of an IL-10 polypeptide can be present in a free form (R1=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic IL-10 Function

It is frequently beneficial, and sometimes imperative, to improve one of more physical properties of the treatment modalities disclosed herein (e.g., IL-10) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications can also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of IL-10 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics is often limited by short plasma half-life and susceptibility to protease degradation. Studies of various therapeutic proteins (e.g., filgrastim) have shown that such difficulties can be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

In addition to the beneficial effects of pegylation on pharmacokinetic parameters, pegylation itself can enhance activity. For example, PEG-IL-10 has been shown to be more efficacious against certain cancers than unpegylated IL-10 (see, e.g., EP 206636A2).

PEGs suitable for conjugation to a polypeptide sequence are generally soluble in water at room temperature, and have the general formula R(O—CH2-CH2)nO—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography can be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114; and Miron and Wilcheck (1993) Bio-conjug. Chem. 4:568-569) and benzotriazole carbonate PEG (BTC-PEG; see, e.g., Dolence, et al. U.S. Pat. No. 5,650,234), which react preferentially with lysine residues to form a carbamate linkage, but are also known to react with histidine and tyrosine residues. The linkage to histidine residues on certain molecules (e.g., IFNα) has been shown to be a hydrolytically unstable imidazolecarbamate linkage (see, e.g., Lee and McNemar, U.S. Pat. No. 5,985,263). Second generation pegylation technology has been designed to avoid these unstable linkages as well as the lack of selectivity in residue reactivity. Use of a PEG-aldehyde linker targets a single site on the N-terminus of a polypeptide through reductive amination.

PEG can be bound to a polypeptide of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide. Another activated polyethylene glycol which can be bound to a free amino group is 2,4-bis(O-methoxypolyethyleneglycol)-δ-chloro-s-triazine, which can be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer can be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions can be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art can be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919, 455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix's XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-10 and can also be important in protein stability, secretion, and subcellular localization. Glycosylated polypeptides can also exhibit enhanced stability or can improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide can be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type can be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, can confer acidic properties to the glycoprotein. A particular embodiment of the present disclosure comprises the generation and use of N-glycosylation variants.

The polypeptide sequences of the present disclosure can optionally be altered through changes at the nucleic acid level, particularly by mutating the nucleic acid encoding the polypeptide at preselected bases such that codons are generated that will translate into the desired amino acids.

Polysialylation: The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300 (1-2):125-30). Various techniques for site-specific polysialylation are available (see, e.g., T. Lindhout et al., PNAS 108(18)7397-7402 (2011)).

Albumin Fusion:

Additional suitable components and molecules for conjugation include albumins such as human serum albumin (HSA), cyno serum albumin, and bovine serum albumin (BSA).

According to the present disclosure, albumin can be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701).

In the HSA-drug molecule conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences.

Alternative Albumin Binding Strategies: Several albumin-binding strategies have been developed as alternatives to direct fusion and can be used with the IL-10 agents described herein. By way of example, the present disclosure contemplates albumin binding through a conjugated fatty acid chain (acylation) and fusion proteins which comprise an albumin binding domain (ABD) polypeptide sequence and the sequence of one or more of the polypeptides described herein.

Conjugation with Other Molecules: Additional suitable components and molecules for conjugation include, for example, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

An IL-10 polypeptide can also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms can, if desired, be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications: The present disclosure contemplates the use of other modifications, currently known or developed in the future, of IL-10 to improve one or more properties. Examples include hesylation, various aspects of which are described in, for example, U.S. Patent Appln. Nos. 2007/0134197 and 2006/0258607, and fusion molecules comprising SUMO as a fusion tag (LifeSensors, Inc.; Malvern, Pa.).

Linkers: Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Examples of flexible linkers include glycine polymers $(G)_n$, glycine-alanine polymers, alanine-serine polymers, glycine-serine polymers (for example, $(G_mS_o)_n$, $(GSGGS)_n$ (SEQ ID NO: 13), $(G_mS_oG_m)_n$ (SEQ ID NO: 14), $(G_mS_oG_m-S_oG_m)_n$ (SEQ ID NO: 15), $(GSGGS_m)_n$(SEQ ID NO: 16), $(GSGS_mG)_n$ (SEQ ID NO:17) and $(GGGS_m)_n$ (SEQ ID NO: 18), and combinations thereof, where m, n, and o are each independently selected from an integer of at least 1 to 20, e.g., 1-18, 2-16, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components. Examples of flexible linkers include, but are not limited to GGSG (SEQ ID NO:19), GGSGG (SEQ ID NO: 20), GSGSG (SEQ ID NO: 21), GSGGG (SEQ ID NO: 22), GGGSG (SEQ ID NO: 23), and GSSSG (SEQ ID NO: 24).

Additional examples of flexible linkers include glycine polymers (G)n or glycine-serine polymers (e.g., $(GS)_n$, $(GSGGS)_n$ (SEQ ID NO:25), $(GGGS)_n$ (SEQ ID NO: 26) and $(GGGGS)_n$ (SEQ ID NO: 27), where n=1 to 50, for example, 1, 2, 3, 4, 5, 6, 7, 8, 9, 10, 10-20, 20-30, 30-50). Exemplary flexible linkers include, but are not limited to GGGS (SEQ ID NO: //), GGGGS (SEQ ID NO: 28), GGSG (SEQ ID NO: 29), GGSGG (SEQ ID NO: 30), GSGSG (SEQ ID NO: 31), GSGGG (SEQ ID NO: 32), GGGSG (SEQ ID NO: 33), and GSSSG (SEQ ID NO: 34). A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the IL-10 agents disclosed herein. As described herein, the heterologous amino acid sequence may be a signal sequence and/or a fusion partner, such as, albumin, Fc sequence, and the like.

IL-10 Agent Administration for Production of PD1+, CD8+ T Cells and for Therapy

To elicit peripheral PD1+, CD8+, disease antigen-specific T cells, an IL-10 agent (e.g., PEG-IL-10) is administered to a subject in a therapeutically effective dose. A therapeutically effective dose may readily be determined by the skilled medical practitioner taking to consideration factors such as the disease to be treated, the goal to be achieved by the therapy, other therapeutic agents that are administered to the subject, as well as a variety of commonly evaluated properties of the subject to be treated such as age, weight, sex, and health and physical condition of the subject the IL-10 agent formulation being administered and the route of administration. Therapeutically effective dosages of IL-10 agents can readily be determined from, for example, safety and dose-escalation trials, in vivo studies (e.g., animal models), and other methods known to the skilled artisan.

As discussed in detail elsewhere, the present disclosure contemplates embodiments wherein administration of IL-10 to achieve certain serum trough concentrations and/or maintain certain mean serum trough concentrations.

In general, dosing parameters dictate that the therapeutically effective dose be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

A therapeutically effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount can be more than the calculated ED50, in other situations the effective amount can be less than the calculated ED50, and in still other situations the effective amount can be the same as the calculated ED50.

Examples of therapeutically effective doses of PEG-IL-10 can range from about 0.01 to about 100 μg PEG-IL-10/kg of body weight/day, from about 0.1 to 20 μg PEG-IL-10/kg of body weight/day, from about 0.5 to 10 μg PEG-IL-10/kg of body weight/day, or about 1 to 4 μg PEG-IL-10/kg of body weight/day. In some embodiments, PEG-IL-10 is administered by continuous infusion to delivery about 50 to 800 μg protein/kg of body weight/day (e.g., about 1 to 16 μg protein/kg of body weight/day of PEG-IL-10). The infusion rate can be varied based on evaluation of, for example, adverse effects and blood cell counts. Other specific dosing parameters for the IL-10 agents are described elsewhere herein.

In certain embodiments, the dose of an IL-10 agent is presented in a "unit dosage form". The phrase "unit dosage form" refers to physically discrete units, each unit containing a predetermined amount of an IL-10 agent, either alone or in combination with one or more additional agents, sufficient to produce the desired effect. It will be appreciated that the parameters of a unit dosage form will depend on the particular agent and the effect to be achieved.

The systemic level of an IL-10 agent can be characterized in several manners, including: (1) a mean IL-10 serum trough concentration above some specified level or in a range of levels; (2) a mean IL-10 serum trough concentration above some specified level for some amount of time; (3) a steady state IL-10 serum concentration level above or below some specified level or in a range of levels; or (4) a $C_{max}$ of the concentration profile above or below some specified level or in some range of levels. As set forth herein, the maintenance of a mean serum trough IL-10 concentrations over the period of administration of the IL-10 agent have been found to be particularly beneficial in the treatment of certain disease states.

In some embodiments of the present disclosure, useful blood plasma and/or serum level concentration profiles of IL-10 agents over the course of IL-10 agent therapy include: a mean IL-10 plasma and/or serum trough concentration of greater than about 1.0 pg/mL, greater than about 10.0 pg/mL, greater than about 20.0 pg/mL, greater than about 30 pg/mL, greater than about 40 pg/mL, greater than about 50.0 pg/mL, greater than about 60.0 pg/mL, greater than about 70.0 pg/mL, greater than about 80.0 pg/mL, greater than about 90 pg/mL, greater than about 0.1 ng/mL, greater than about 0.2 ng/mL, greater than about 0.3 ng/mL, greater than about 0.4 ng/mL, greater than about 0.5 ng/mL, greater than about 0.6 ng/mL, greater than about 0.7 ng/mL, greater than about 0.8 ng/mL, greater than about 0.9 ng/mL, greater than about 1.0 ng/mL, greater than about 1.5 ng/mL, greater than about 2.0 ng/mL, greater than about 2.5 ng/mL, greater than about 3.0 ng/mL, greater than about 3.5 ng/mL, greater than about 4.0 ng/mL, greater than about 4.5 ng/mL, greater than about 5.0 ng/mL, greater than about 5.5 ng/mL, greater than about 6.0 ng/mL, greater than about 6.5 ng/mL, greater than about 7.0 ng/mL, greater than about 7.5 ng/mL, greater than about 8.0 ng/mL, greater than about 8.5 ng/mL, greater than about 9.0 ng/mL, greater than about 9.5 ng/mL, or greater than about 10.0 ng/mL.

In particular embodiments of the present disclosure, the IL-10 agents is administered to a subject to achieve a mean IL-10 serum trough concentration over the course of IL-10 treatment in the range of from 1.0 pg/mL to 10 ng/mL, alternatively in the range of from 1.0 pg/mL to 100 pg/mL, alternatively in the range of from 0.1 ng/mL to 1.0 ng/mL, alternatively in the range of from 1.0 ng/mL to 10 ng/mL. It is to be understood that the present disclosure contemplates ranges incorporating any concentrations encompassed by those set forth herein even if such ranges are not explicitly recited. By way of example, the mean serum IL-10 concentration in an embodiment can be in the range of from 0.5 ng/mL to 5 ng/mL. By way of further examples, particular embodiments of the present disclosure comprise a mean IL-10 serum trough concentration in a range of from about 0.5 ng/mL to about 10.5 ng/mL, from about 1.0 ng/mL to about 10.0 ng/mL, from about 1.0 ng/mL to about 9.0 ng/mL, from about 1.0 ng/mL to about 8.0 ng/mL, from about 1.0 ng/mL to about 7.0 ng/mL, from about 1.5 ng/mL to about 10.0 ng/mL, from about 1.5 ng/mL to about 9.0 ng/mL, from about 1.5 ng/mL to about 8.0 ng/mL, from about 1.5 ng/mL to about 7.0 ng/mL, from about 2.0 ng/mL to about 10.0 ng/mL, from about 2.0 ng/mL to about 9.0 ng/mL, from about 2.0 ng/mL to about 8.0 ng/mL, and from about 2.0 ng/mL to about 7.0 ng/mL. In particular embodiments, a mean IL-10 serum trough concentration of 1-2 ng/mL is maintained over the duration of treatment.

The present disclosure also contemplates embodiments wherein the mean IL-10 serum peak concentration is less than or equal to about 10.0 ng/mL over the duration of IL-10 agent treatment. Further embodiments contemplate a mean IL-10 serum trough concentration greater than or equal to about 1.0 pg/mL. The optimal mean serum concentration is generally that at which the desired therapeutic effect is achieved without introducing undesired adverse effects.

Certain embodiments of the present disclosure provide a method for monitoring a subject receiving IL-10 therapy to predict, and thus potentially avoid, adverse effects, the method comprising: (1) measuring the subject's peak concentration of IL-10; (2) measuring the subject's trough concentration of IL-10; (3) calculating a peak-trough fluctuation; and, (4) using the calculated peak-trough fluctuation to predict potential adverse effects in the subject. In particular subject populations, a smaller peak-trough fluctuation indicates a lower probability that the subject will experience IL-10-related adverse effects. In addition, in some embodiments, particularly peak-trough fluctuations, are determined for the treatment of particular diseases, disorders and conditions using particular dosing parameters and those fluctuations are used as reference standards.

For the majority of drugs, plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. Intravenous IL-10 administration is associated with such a two-compartment kinetic model (see Rachmawati, H. et al. (2004) Pharm. Res. 21(11):2072-78). The pharmacokinetics of subcutaneous recombinant hIL-10 has also been studied (Radwanski, E. et al. (1998) Pharm. Res. 15(12):1895-1901). Thus, volume-of-distribution considerations are pertinent when assessing appropriate IL-10 dosing-related parameters. Moreover, efforts to target IL-10 agents to specific cell types have been explored (see, e.g., Rachmawati, H. (May 2007) Drug Met. Dist. 35(5):814-21.

The present disclosure contemplates administration of any dose and dosing regimen of an IL-10 agent that results in maintenance of any of the IL-10 serum trough concentrations in the subject being treated as set forth above. By way of example, but not limitation, when the subject is a human, non-pegylated hIL-10 can be administered at a dose greater than 0.5 µg/kg/day, greater than 1.0 µg/kg/day, greater than 2.5 µg/kg/day, greater than 5 µg/kg/day, greater than 7.5 µg/kg, greater than 10.0 µg/kg, greater than 12.5 µg/kg, greater than 15 µg/kg/day, greater than 17.5 µg/kg/day, greater than 20 µg/kg/day, greater than 22.5 µg/kg/day, greater than 25 µg/kg/day, greater than 30 µg/kg/day, or greater than 35 µg/kg/day. In addition, by way of example, but not limitation, when the subject is a human, pegylated hIL-10 comprising a relatively small PEG (e.g., 5 kDa mono-di-PEG-hIL-10) can be administered at a dose greater than 0.5 µg/kg/day, greater than 0.75 µg/kg/day, greater than 1.0 µg/kg/day, greater than 1.25 µg/kg/day, greater than 1.5 µg/kg/day, greater than 1.75 µg/kg/day, greater than 2.0 µg/kg/day, greater than 2.25 µg/kg/day, greater than 2.5 µg/kg/day, greater than 2.75 µg/kg/day, greater than 3.0 µg/kg/day, greater than 3.25 µg/kg/day, greater than 3.5 µg/kg/day, greater than 3.75 µg/kg/day, greater than 4.0 µg/kg/day, greater than 4.25 µg/kg/day, greater than 4.5 µg/kg/day, greater than 4.75 µg/kg/day, or greater than 5.0 µg/kg/day.

Although the preceding discussion regarding IL-10 serum concentrations, doses and treatment protocols that are necessary to achieve particular IL-10 serum concentrations, etc., pertains to monotherapy with an IL-10 agent (e.g., PEG-IL-10), the skilled artisan (e.g., a pharmacologist) is able to determine the optimum dosing regimen(s) when an IL-10 agent (e.g., PEG-IL-10) is administered in combination with one or more additional therapies.

Routes of Administration

The present disclosure contemplates the administration of the IL-10 agent (e.g., PEG-IL-10), and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, can also be utilized to release the IL-10 agents disclosed herein over a defined period of time.

Methods for Producing Disease Antigen-Specific PD1+ CD8+ Peripheral T Cells

As noted above, the present disclosure provides, in one embodiment, a method of inducing expansion of disease antigen-specific CD8+ T cells into the periphery of a subject having a disease treatable with an IL-10 agent therapy by the administration of a therapeutically effective amount of an IL-10 agent to the patient. Further, disease antigen-specific CD8+ T cells may be isolated by obtaining a tissue sample from the subject following the administration of a therapeutically effective dose of an IL-10 agent to the subject. In one embodiment, the antigen-specific CD8+ T cells are PD1+ (e.g., PD1mid-high), CD8+ T cells are obtained from a subject treated with a therapeutically effective dose of an IL-10 agent by obtaining a sample of peripheral blood from the subject.

Figure 7:
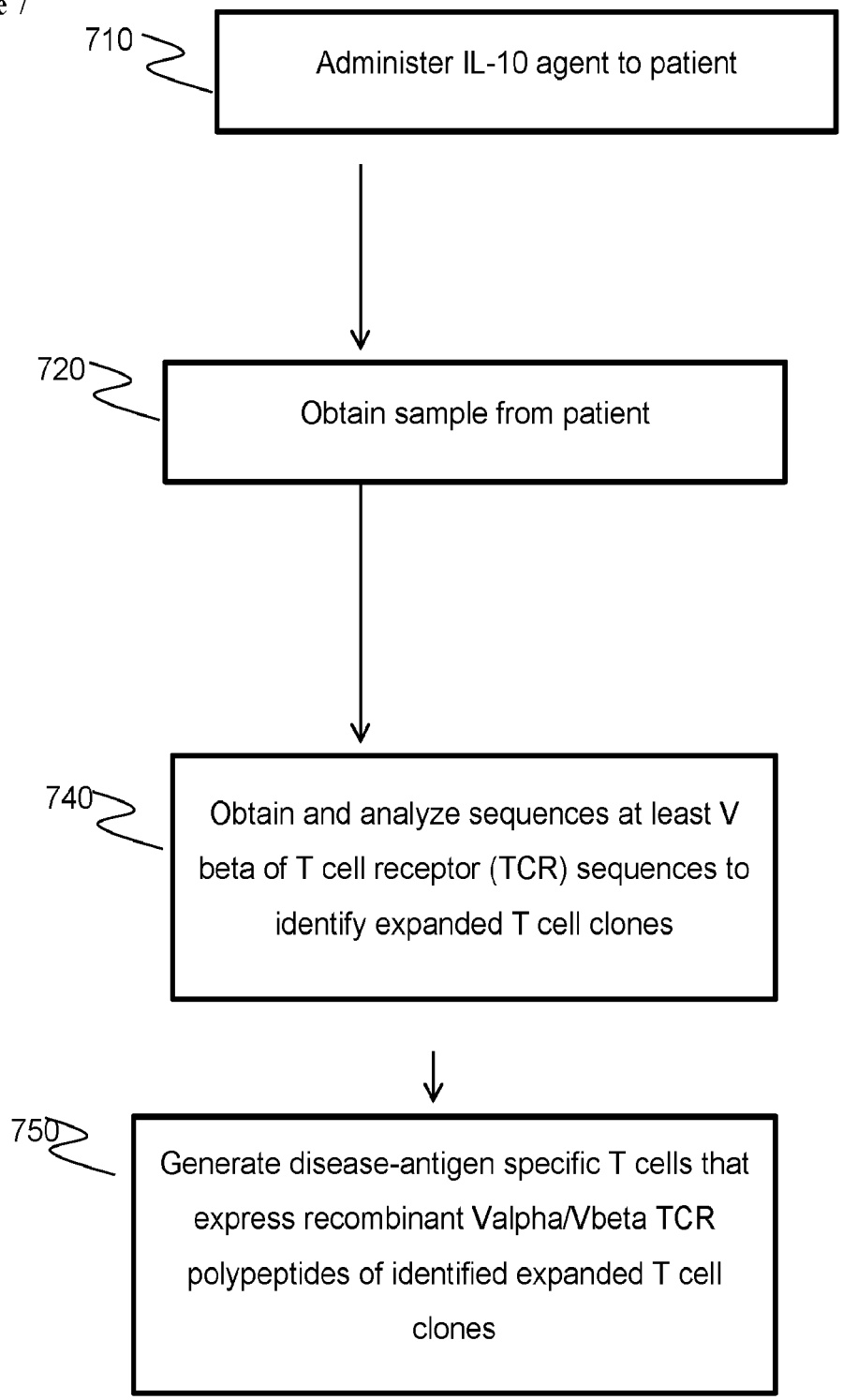
FIG. 7 is a schematic of production of PD1+, CD8+ disease antigen-specific T cells obtained from a subject treated with an IL-10 agent.

With reference to FIG. 7, an example of a general implementation of a method of the present disclosure may include administering 710 an IL-10 agent therapy, e.g., PEG-IL-10 therapy, to a patient having a disease that is amenable to treatment by an IL-10 agent. After the patient has received the IL-10 agent therapy for a predetermined amount of time, a tissue sample containing lymphocytes, (e.g., a peripheral blood sample containing peripheral blood lymphocytes (PBLs)), is collected from the patient 720. Optionally, the patient may be monitored for response to the IL-10 agent therapy. In some cases, the tissue sample is collected from the patient if the patient demonstrates at least a stable disease state or at least a partial response to the IL-10 agent therapy. In some cases, if the patient does not show at least stable disease or at least a partial response, the IL-10 agent therapy is continued without collecting the tissue sample.

After collecting 720 the tissue sample from the patient, nucleic acids in the tissue sample are analyzed by nucleic acid sequencing 740 to obtain TCR sequences (e.g., nucleic acids encoding a variable alpha (Vα) TCR polypeptide and/or nucleic acids encoding a variable beta (Vβ) TCR polypeptide). The sequences may be analyzed to obtain an estimate of the [relative] abundance of nucleic acids encoding the Vα TCR polypeptide and/or nucleic acids encoding the Vβ TCR polypeptide for TCRs expressed on CD8+ T cells. By comparing the abundance of nucleic acids encoding the Vα TCR polypeptide and/or nucleic acids encoding the Vβ TCR polypeptide for TCRs expressed on CD8+ T cells in the sample with the abundance of the nucleic acids encoding the Vα TCR polypeptide and/or nucleic acids encoding Vβ TCR polypeptide in a reference sample obtained from one or more patients having the disease amenable to IL-10 agent therapy either prior IL-10 agent therapy or at an earlier time point during IL-10 agent therapy, it is possible to determine whether a particular T cell population expressing an antigen-specific TCR (defined by the α chain and β chain TCR pair sequences) has clonally expanded, clonally contracted, or has been newly generated in response to the IL-10 agent therapy.

The abundance of a nucleic acid encoding the Vα TCR polypeptide and/or nucleic acids encoding Vβ TCR polypeptide in a sample may be determined using any suitable measure. In some cases, the abundance is a frequency of the nucleic acid encoding the Vα TCR polypeptide and/or nucleic acids encoding Vβ TCR polypeptide relative to a reference nucleic acid. In some cases, the abundance is a number, or a bioinformatically obtained estimate thereof, of the nucleic acid encoding the Vα TCR polypeptide and/or nucleic acids encoding Vβ TCR polypeptide relative to a reference nucleic acid.

An expansion may include a change in the abundance of the Vα TCR polypeptide and/or nucleic acids encoding Vβ TCR polypeptide in the sample from the subject compared to a reference sample of 3 fold or more, e.g., 5 fold or more, 10 fold or more, 20 fold or more, or 30 fold of more.

In some cases, the sample contains PBLs, which may be fractionated based on cell surface marker expression, to isolate antigen-specific CD8+ T cells of interest. The CD8+ T cells of interest may include activated, disease antigen-specific CD8+ T cells, identified based on elevated expression of cell surface markers, such as PD1 (CD279) and/or LAG3. In some embodiments, the method may optionally include identifying and isolating PD1+CD8+ T cells and/or PD-1+ Lag3+CD8+ T cells from the peripheral blood sample. In one embodiment, the T cells are identified and isolated as being PD1mid-high, CD8+, as well as positive for expression of one or more of IFNγ, CD45RO, Granzyme B, and Perforin. The isolated CD8+ T cells, e.g., PD1+CD8+ T cells, may be enriched in activated T cells that are specific to disease-associated antigens, which disease antigen specificity is in turn governed by the α chain and β chain TCR pair sequences.

These TCR pair amino acid sequences may include sequences that confer disease antigen specificity to T cells. Thus, in some embodiments, a method of the present disclosure includes generating recombinant disease antigen-specific T cells 750 by transducing nucleic acid constructs encoding full-length α chain and β chain TCR pair amino sequences, or chimeric antigen receptor containing the variable regions of the α chain and β chain TCR pair amino sequences, where the α chain and β chain TCR pair amino acid sequences were derived from disease antigen-specific T cell-containing tissue samples obtained from the patient treated with an IL-10 agent. These engineered disease antigen-specific T cells may then be administered to a suitable patient in need of treatment for diseases characterized by the expression of antigens specifically bound by the TCR expressed on the engineered disease antigen-specific T cell.

A method of the present disclosure may include obtaining a population of disease antigen-specific CD8+ T cells from a patient to whom an IL-10 agent has been administered to treat a condition. The patient may be any individual who has a condition, e.g., a disease, that is responsive to an IL-10 agent therapy, i.e., a condition in which the antigen-reactive cytotoxic activity of CD8+ T cells contributes to amelioration of the condition.

The patient may have any condition that is responsive to an IL-10 agent therapy, including, without limitation, cancers; cholesterol related diseases, and diseases caused by infectious agents, such as viruses, bacteria, fungi, protozoans and parasites with an intracellular life cycle.

According to the methods described herein, the condition or disease may be a proliferative disorder, such as cancer or a cancer-related disorder. Though not limited to particular cancers, the cancer may be a solid tumor, including tumors associated with colon cancer, melanoma, and squamous cell carcinoma, or it may be a hematological disorder. The patient may have a proliferative condition or disease, including, but not limited to, a cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, skin, liver, gall bladder, heart, lung, pancreas, salivary gland, adrenal gland, thyroid, brain (e.g., gliomas), ganglia, central nervous system (CNS) and peripheral nervous system (PNS); and cancers of the hematopoietic system and the immune system (e.g., spleen or thymus). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia. In some embodiments, the cancer is metastatic.

Viral infectious agents include single-stranded DNA (ssDNA), double-stranded DNA (dsDNA) and RNA viruses. In some embodiments, the virus is a hepadnavirus, flavivirus, retrovirus, or herpes virus. In some cases, the patient has a viral infection caused by, without limitation, hepatitis type A, hepatitis type B (HBV), hepatitis type C (HCV), influenza, varicella-zoster virus (VZV), adenovirus, Epstein-Barr virus (EBV), herpes simplex type I (HSV-I), herpes simplex type II (HSV-II), rhinovirus, echovirus, rotavirus, respiratory syncytial virus, human papilloma virus (HPV), papova virus, cytomegalovirus (CMV), echinovirus, arbovirus, huntavirus, coxsachie virus, mumps virus, measles virus, rubella virus, polio virus, human immunodeficiency virus type I (HIV-I), and human immunodeficiency virus type II (HIV-II), human T lymphotropic viruses (HTLV-1 and HTLV-2), coronavirus, poliomyelitis virus, human herpes virus 6 (HHV-6), etc.

In some embodiments, the patient is a subject to whom an IL-10 agent has been administered, as described further below, and whose condition shows at least a partial clinical response to the IL-10 agent treatment. The clinical response to the treatment may be measured using any suitable method, and will vary with the condition treated.

For example, where the condition is a tumor, the response of a subject to IL-10 agent treatment is obtained by measuring, for example, the tumor load (e.g., tumor mass, tumor volume, amount of tumor biomarkers, etc.) and/or the tumor distribution, before and after the treatment. A "partial clinical response" of subject having cancer to IL-10 agent treatment generally refers to a decrease in the size of a tumor, or in the extent of cancer in the body of the patient, and may include 10% or more, e.g., 20% or more, 30% or more, 40% or more, including 50% or more, and 99% or less, e.g., 90% or less, 80% or less, 70% or less, including 60% or less, reduction in the measured clinical variable (e.g., tumor volume and/or tumor mass) after the treatment compared to before the treatment, where 100% reduction may represent reduction of the measured clinical variable to undetectable levels and/or background levels. A background level of the condition may be an average measurement of the clinical variable for the condition that is obtained in individuals who are known not to have the condition. In contrast, a cancer subject is referred to as exhibiting "stable disease" following IL-10 agent therapy where the cancer neither decreases nor increases in extent or severity as measured by a selected clinical variable (e.g., such as tumor volume and/or tumor mass). A cancer subject is classified as a "non-responder" to therapy following IL-10 agent therapy where the cancer increases in extent or severity as measured by a selected clinical variable (e.g., such as tumor volume and/or tumor mass).

In some embodiments, the response of a viral infectious disease to the IL-10 agent treatment is obtained by comparing relevant clinical measurements, for example, a viral titer (e.g., in blood), anti-viral antibodies (e.g., in blood), levels of viral-derived nucleic acids (e.g., in the blood or tissue, e.g., as detected by PCR), before and after IL-10 agent treatment. A "partial clinical response" of a viral infection to the IL-10 agent treatment may include 10% or more, e.g., 20% or more, 30% or more, 40% or more, including 50% or more, and 99% or less, e.g., 90% or less, 80% or less, 70% or less, including 60% or less, reduction in the measured clinical variable (e.g., viral titer, virus-specific antibody titer and/or viral protein titer) after the treatment compared to before the treatment, where 100% reduction may represent reduction of the measured clinical variable to undetectable levels and/or background levels. For example, in some embodiments, an at least partial clinical response to IL-10 agent therapy can be one or more of an at least 90% reduction of viral nucleic acid detectible by qPCR in the blood or a blood fraction (serum/plasma); an at least 90% decrease in antibody titers to a known viral antigen(s); an at least 90% reduction of viral proteins in the serum (e.g., as detected by ELISA). A background level of the condition may be an average measurement of the clinical variable for the condition that is obtained in individuals who are known not to have the condition.

The IL-10 agent therapy may be any suitable IL-10 agent therapy as described above for treating the condition, and includes administering a therapeutically effective amount of an IL-10 agent to the patient. Suitable IL-10 agents include recombinant human IL-10 and pegylated IL-10, and are described in e.g., U.S. Pat. No. 6,217,857; US 2008/0317707; and U.S. Pat. No. 8,691,205. In some embodiments, the IL-10 agent is a mixture of pegylated IL-10s, such as a mono-pegylated IL-10 and a di-pegylated-IL10, e.g., as described in U.S. Pat. No. 8,691,205. The administration regimen may include any suitable dosage, dosing interval, and dosing period to achieve a therapeutic effect on the condition, e.g., cancer or infectious disease. In some cases, the administration regimen includes a dosage of the IL-10 agent of 0.1 µg/Kg or more, e.g., 0.5 µg/Kg or more, 1.0 µg/Kg or more, 2.0 µg/Kg or more, 5.0 µg/Kg or more, including 10 µg/Kg or more, and a dosage of 50 µg/Kg or less, e.g., 40 µg/Kg or less, 30 µg/Kg or less, including 20 µg/Kg or less. In some cases, the administration regimen includes a dosage of the IL-10 agent in the range of 0.1 to 50 µg/Kg, 0.5 to 40 µg/Kg, 1.0 to 40 µg/Kg, including 10 to 40 µg/Kg.

In some cases, the administration regimen of the IL-10 agent includes dosing at an interval of once a week or shorter, e.g., once every three days or shorter, once every two days or shorter, including once every day or shorter, and an interval of three times a day or longer, e.g., twice a day or longer, including once a day or longer. In some cases, the administration regimen includes dosing at an interval in the range of three times a day to once a week, e.g., twice a day to once every three days, including twice a day to once every two days. In some cases, the IL-10 therapy has been administered to the patient for at least 1-150 days, at least 5-100 days, at least 10-50 days, at least 15-45 days, at least 20-40 days, at least 30 days or more, and may have been administered for 1 day, 2 days, 3, days, 4, days, 5, days 6, days, 7, days, 8 days, 9, days, 10 days, 11 days, 12 days, 13 days, 14 days, 15 days, 16 days, 17 days, 18 days, 19 days, 20 days, 21 days, 22 days, 23 days, 24 days, 25 days, 26 days 27 days, 28 days, or 29 days or more. In some cases, IL-10 agent will have been administered for several weeks, e.g., 3 weeks or more, 4 weeks or more, 5 weeks or more, 6 weeks or more, 2 months or more, including 3 months or more, and for 5 years or less, e.g., 1 year or less, 9 months or less, 6 months or less, including 3 months or less. In some embodiments, the IL-10 therapy has been administered to the patient between 2 weeks to 5 years, e.g., 3 weeks to 1 year, 4 weeks to 9 months, including 4 weeks to 6 months.

The tissue sample obtained from the patient treated with an IL-10 agent therapy, as described above, may be any suitable tissue sample that contains CD8+ T cells. In some cases, the tissue sample is a tumor sample, such as a sample from a primary tumor or a metastasis thereof. In some embodiments, the sample is a peripheral blood sample. In some embodiments, peripheral CD8+ T cells are isolated from a sample, e.g., a peripheral blood sample, obtained from the patient. As used herein, "peripheral blood" refers to blood circulating within an individual's circulatory system. A peripheral blood sample may be obtained directly from the circulating pool of blood. According to aspects of the present disclosure, a population of peripheral CD8+ T cells may be obtained from the patient treated with the IL-10 agent, as described above, using any suitable method (see, e.g., Fuss et al. (2009) Current Protocols in Immunology, Unit 7.1, John Wiley, Inc. NY). In some embodiments, the sample is a lymph node sample, or a lymph sample.

The patient test sample, as well as any suitable patient reference sample, containing CD8+ T cells may be obtained from the patient at any suitable time. In some embodiments, it may be of interest to obtain the reference sample prior to initiation of IL-10 agent therapy and the test sample after initiation of therapy. Test samples obtained at point after the patient's condition is is at least stable (stable disease) or exhibits at least a partial clinical response (PR) to IL-10 agent therapy. Time points for obtaining test samples (and/or reference samples where analysis of the effect of continued IL-10 agent therapy upon T cell expansion is of interest) include but are not limited to: be within or after 1 day, 2 days, 3 days, 4, days, 5, days 6, days, 7, days, 8 days, 9, days, 10 days, 11 days, 12 days, 13 days, 14 days, 15 days, 16 days, 17 days, 18 days, 19 days, 20 days, 21 days, 22 days, 23 days, 24 days, 25 days, 26 days 27 days, 28 days, or 29 days or more of initiation of therapy, and may be, for example, 1-200 days, 10-190 days, 20-180 days after initiation of therapy. In some cases, the sample containing CD8+ T cells may be obtained from the patient following IL-10 agent administration for several weeks, e.g., 3 weeks or more, 4 weeks or more, 5 weeks or more, 6 weeks or more, 2 months or more, including 3 months or more, and for 5 years or less, e.g., 1 year or less, 9 months or less, 6 months or less, including 3 months or less. In some embodiments, the IL-10 therapy has been administered to the patient between 2 weeks to 5 years, e.g., 3 weeks to 1 year, 4 weeks to 9 months, including 4 weeks to 6 months prior to obtaining the sample containing CD8+ T cells.

In some cases, the sample obtained from the patient may be processed in any convenient manner to isolate the CD8+ T cells, e.g., peripheral CD8+ T cells. In some cases, lymphocytes, e.g., peripheral blood lymphocytes (PBLs), in the sample are sorted or fractionated to provide one or more samples containing populations of CD8+ T cells enriched for specific CD8+ T cell subtypes (e.g., PD1mid-high, CD8+ T cells), based on the expression of cell-surface markers on the lymphocytes, e.g., on the PBLs. The sorting or fractionating may be done using any suitable method, e.g., fluorescence activated cell sorting (FACS), magnetic bead-based separation, etc.

The population of CD8+ T cells contained in the sample and/or isolated from the sample obtained from the patient may be enriched for any suitable CD8+ T cells that are activated and are antigen-specific. As discussed above, T cells may exhibit a substantially bimodal distribution of a cell surface marker expression, e.g., PD1 (also known as CD279) cell surface expression. Thus, where the activated T cells are identified based on surface expression of PD1, cells around the higher peak of PD1 cell surface expression may be classified as "PD1high" and cells around the lower peak of PD1 cell surface expression may be classified as "PD1low". The population of CD8+ T cells that include activated CD8+ T cells may also include an intermediate population of cells (PD1mid) in between PD1high and PD1low cells, where PD1mid cells have a level of PD1 cell surface expression that is higher than PD1 low cells, but lower than PD1 high cells. Thus, activated, antigen-specific CD8+ T cells of interest may include an intermediate-to-high level of cell surface expression of PD1 ("PD1mid-high"). In other words, the activated, antigen-specific CD8+ T cells may be a population of CD8+ T cells that do not have a low expression of PD1 on the cell surface (i.e., that are not "PD1low").

The level of expression of a cell surface marker, e.g., PD1, may be measured, and cells having a level of expression of the cell surface marker that falls within a desired range may be isolated using any suitable method, such as, but not limited to, labeling of cells with fluorescently-detectable antibodies to the cell surface marker, followed by FACS; or magnetic bead-based separation, etc.

Antigen-specific CD8+ T cells may be defined by any other suitable marker for antigen-specific CD8+ T cells. In some embodiments, antigen-specific CD8+ T cells exhibit elevated cell surface expression of CD45RO ("CD45RO+"). In some embodiments, antigen-specific CD8+ T cells have a high level of expression of interferon (IFN) γ ("IFNγ+"). In some embodiments, antigen-specific CD8+ T cells exhibit elevated expression of Granzyme B and/or Perforin, which are markers of T cell activation. Thus, the present disclosure contemplates samples enriched for PD1 and CD8 cell surface expression, as well as any combination of other markers, for example:

1) PD1+(e.g., PD1mid-high), CD8+, CD45RO+;
2) PD1+(e.g., PD1mid-high), CD8+, IFNγ+;
3) PD1+(e.g., PD1mid-high), CD8+, CD45RO+, Granzyme B+;
4) PD1+(e.g., PD1mid-high), CD8+, CD45RO+, Perforin+;
5) PD1+(e.g., PD1mid-high), CD8+, CD45RO+, Granzyme B+, Perforin+;
6) PD1+(e.g., PD1mid-high), CD8+, IFNγ+, Granzyme B+;
7) PD1+(e.g., PD1mid-high), CD8+, IFNγ+, Perforin+;
8) PD1+(e.g., PD1mid-high), CD8+, IFNγ+, Granzyme B+, Perforin+;
9) PD1+(e.g., PD1mid-high), CD8+, Granzyme B+;
10) PD1+(e.g., PD1mid-high), CD8+, Granzyme B+, Perforin+;
11) PD1+(e.g., PD1mid-high), CD8+, Perforin+; or
12) PD1+(e.g., PD1mid-high), CD8+, IFNγ+, CD45RO+, Granzyme B+, Perforin+.
13) LAG3+(e.g., LAG3 mid-high), CD8+, CD45RO+;
14) LAG3+(e.g., LAG3 mid-high), CD8+, IFNγ+;
15) LAG3+(e.g., LAG3 mid-high), CD8+, CD45RO+, Granzyme B+;
16) LAG3+(e.g., LAG3 mid-high), CD8+, CD45RO+, Perforin+;
17) LAG3+(e.g., LAG3 mid-high), CD8+, CD45RO+, Granzyme B+, Perforin+;
18) LAG3+(e.g., LAG3 mid-high), CD8+, IFNγ+, Granzyme B+;
19) LAG3+(e.g., LAG3 mid-high), CD8+, IFNγ+, Perforin+;
20) LAG3+(e.g., LAG3 mid-high), CD8+, IFNγ+, Granzyme B+, Perforin+;
21) LAG3+(e.g., LAG3 mid-high), CD8+, Granzyme B+;
22) PD1+(e.g., PD1mid-high), CD8+, Granzyme B+, Perforin+;
23) PD1+(e.g., PD1mid-high), CD8+, Perforin+; or
24) PD1+(e.g., PD1mid-high), CD8+, IFNγ+, CD45RO+, Granzyme B+, 25) PD1+, LAG3+, CD8+, CD45RO+;
26) PD1+, LAG3+, CD8+, IFNγ+;
27) PD1+, LAG3+, CD8+, CD45RO+, Granzyme B+;
28) PD1+, LAG3+, CD8+, CD45RO+, Perforin+;
29) PD1+, LAG3+, CD8+, CD45RO+, Granzyme B+, Perforin+;
30) PD1+, LAG3+, CD8+, IFNγ+, Granzyme B+;
31) PD1+, LAG3+, CD8+, IFNγ+, Perforin+;
32) PD1+, LAG3+, CD8+, IFNγ+, Granzyme B+, Perforin+;
33) PD1+, LAG3+, CD8+, Granzyme B+;
34) PD1+, LAG3+, CD8+, Granzyme B+, Perforin+;
35) PD1+, LAG3+, CD8+, Perforin+; or
36) PD1+, LAG3+, CD8+, IFNγ+, CD45RO+, Granzyme B+, Other suitable cell surface markers whose expression may be used to sort and enrich for activated and/or antigen-specific CD8+ T cells includes, without limitation, one or more of LAG-3, TIM-3, 4-1BB, CTLA-4 and ICOS (see, e.g., Gros et al., *J Clin Invest.* 2014 May; 124(5):2246-59).

Analysis of TCRs of Disease Antigen-Specific, CD8+ T Cells and Production of Libraries Sequencing.

In a further aspect, a method of the present disclosure includes sequencing nucleic acids containing nucleotide sequences that encode alpha and beta chains of the T cell receptor (TCR) from the sample containing antigen-specific (e.g., PD1+ and/or LAG3+) CD8+ T cells. The sequencing may be carried out using any suitable method that can determine the amino acid sequence of at least the complementarity determining regions (CDRs) in the variable regions of an alpha and beta chain pair that make up a functional, antigen-specific TCR expressed in the sample containing CD8+ T cells, e.g., isolated CD8+ T cells. Suitable methods are described in, e.g., US 20140322716, US 20130273647, US 20150031043. (See also, e.g., Howie et al. "High-throughput pairing of T cell receptor α and β sequences." *Science translational medicine* 7.301 (2015): 301ra131-301ra131.)

In some embodiments, the sequencing may include using high-throughput sequencing platforms (such as Roche 454 (e.g., Roche 454 GS FLX); Applied Biosystems' SOLiD® system (e.g., SOLiD® v4); Illumina's GAIIx, HiSeq® 2000 and MiSeq® sequencers; Life Technologies' Ion Torrent® semiconductor sequencing platform, Pacific Biosciences' PacBio RS and Sanger's 3730xl); suitable primer pairs designed to amplify diverse TCR sequences; and suitable computational algorithms, to determine pairs of alpha and beta chains expressed on individual CD8+ T cells, e.g., isolated CD8+ T cells. Suitable methods are described in, e.g., US 20140322716, US 20150031043, each of which are incorporated herein by reference.

In some embodiments, the sequencing may include sorting individual cells of the population of CD8+ T cells, e.g., isolated CD8+ T cells, and determining the sequence of nucleotide sequences encoding alpha and beta chains of the TCR expressed in the individually sorted CD8+ T cells, e.g., isolated CD8+ T cells (see, e.g., US 20130273647; Kobayashi et al., Nat Med. 2013 November; 19(11):1542-δ).

In some embodiments, the CD8+ T cells, e.g., isolated PD1+CD8+ T cells, may be cultured in vitro to expand and/or select the population of isolated CD8+ T cells obtained from the patient before sequencing nucleic acids from the T cells. Any suitable method may be used to expand and/or select the population of isolated antigen-specific CD8+ T cells in culture.

After sequencing nucleic acids encoding paired alpha and beta chain of a TCR expressed on the surface of CD8+ T cells, e.g., isolated CD8+ T cells, the amino acid sequence of the alpha and beta chains, including the CDR regions of each chain, may be determined.

In some embodiments, a method of the present disclosure may include analyzing the amino acid sequences of the paired alpha and beta chains of the TCR expressed on the surface of CD8+ T cells, e.g., isolated CD8+ T cells determined by a method, as described above. In some embodiments, the analyzing may include comparing the paired alpha and beta chains of the TCR sequences derived from periphery blood of IL-10 agent-treated patients with similar, paired alpha and beta chains of the TCR sequences derived from the site of the pathology in the patient before the IL-10 agent treatment. Such an analysis may reveal one or more antigen-specific TCRs that are expressed on T cells that are preferentially expanded due to the IL-10 agent treatment. The site of the pathology may be, e.g., a tumor, or a site of an infection, and T cells infiltrating the site of the pathology may be obtained from a biopsy from the patient before the IL-10 agent treatment.

In some cases, the analyzing may include comparing a plurality of clonal alpha and/or beta chain amino acid sequences from one or more patients, and generating a consensus primary structure of the alpha and/or beta chain for TCRs specific to a known, or unknown, disease-associated antigen. The consensus primary structure may include any feature of the amino acid sequence that varies depending on the amino acid position in the primary structure, where the feature may be relevant to the antigen specificity. Consensus primary structures of interest include, but not limited to, a consensus charge distribution along the length of the alpha and/or beta chain, and a consensus amino acid sequence of the alpha and/or beta chain.

In some cases, analyzing the amino acid sequences of the paired alpha and beta chains of the TCR expressed on the surface of CD8+ T cells, e.g., isolated CD8+ T cells, may include comparing a plurality of clonal alpha and/or beta chain amino acid sequences from multiple patients, and generating a consensus primary structure of the alpha and/or beta chain for TCRs based on one or more parameters of the sample. The parameters may be any suitable parameter of the sample, including, but not limited to, a haplotype of the patients, the type of disease (e.g., type of cancer, type of infection) the patient has, etc. For example, in some cases, analyzing the amino acid sequences may reveal that a patient has a clonal alpha and/or beta chain amino acid sequence to a disease or disease antigen that is unique to the patient (i.e., a "private" T cell response). In some cases, analyzing the amino acid sequences may reveal that two or more patients each have similar clonal alpha and/or beta chain amino acid sequences to a disease or disease antigen (i.e., a "public" T cell response).

Analyzing for consensus sequences among the amino acid sequences of the paired alpha and beta chains of the TCR expressed on the surface of CD8+ T cells, e.g., isolated CD8+ T cells may be done using any convenient method. Suitable methods are described in, e.g., Khan, et al. *Journal of Infectious Diseases* 185.8 (2002): 1025-1034; Trautmann, et al. *European journal of immunology* 32.11 (2002): 3181-3190. Typically the analysis of the amino acid sequences is performed over regions of the alpha and beta chains of the TCR that contributes to antigen specificity of the TCR. In some cases, the analyzing is performed with respect to one or more complementarity determining regions (CDRs, such as CDR1, CDR2 and/or CDR3) of the variable regions of one or both of the alpha and beta chains (Vα and Vβ) of the TCR. In some cases, the analyzing is performed with respect to the variable regions of the alpha and beta chains of the TCR. In some cases, the analyzing is performed with respect to regions of the alpha and beta chains of the TCR that include the variable and constant regions (i.e., the full length alpha and beta chain TCR polypeptides). In some cases, the analyzing is performed with respect to full-length alpha and beta chains of the TCR.

Analysis of Antigen Specificity.

In some embodiments, the CD8+ T cells, e.g., isolated CD8+ T cells, may be further sorted to identify and isolate those cells that are specific to a known antigen, e.g., a known disease antigen, or specific for a novel antigen present in diseased tissue of the patient from whom the T cells were obtained.

In some embodiments, the methods of the present disclosure can be used to identify new disease antigen-specific TCR alpha/beta pairs and/or new disease-specific antigens. In such embodiments, disease antigen specificity can be assessed by obtaining a sample of diseased tissue containing patient CD8+ T cells (e.g., a solid tumor biopsy) from the patient prior to IL-10 agent treatment. This pretreatment sample can serve as an archival sample. This pretreatment sample can be subjected to the same treatment and analysis of as post-treatment samples as described herein, and the TCR alpha and beta sequences in the pretreatment sample obtained. The TCR sequences present in the pretreatment sample can then be compared with the TCR sequences of the posttreatment sample(s) (e.g., taken at different time points following initiation of IL-10 agent therapy) to identify TCR alpha and beta sequences present in diseased tissue T cells prior to IL-10 agent therapy and after IL-10 agent therapy (e.g., at different time points, e.g., at day 1 compared to one or more of day 1, day 5, day 10, day 15, day 20, day 30, and the like). TCR alpha and/or beta sequences that are increased in frequency following IL-10 agent therapy are identified as TCRs of CD8+ T cells that expanded in response to IL-10 agent therapy and are specific for an antigen of the diseased tissue (e.g., tumor antigen-specific).

Disease antigen binding specificity can be analyzed by, for example, identifying TCRs present on T cells in the patient that expanded following IL-10 agent therapy. For example, the amino acid sequences, or encoding nucleic acid sequences, of Vα and/or Vβ TCR polypeptides present in a sample of diseased tissue or disease associated tissue containing patient CD8+ T cells (e.g., a solid tumor biopsy, virally-infected tissue, and the like) is obtained from the patient prior to IL-10 agent treatment. This pretreatment sample can serve as an archival sample. It should be noted that since the pretreatment sample is used as a source for TCR-related sequences, it is not necessary to subject this sample to selection for T cells.

The encoding nucleic acid sequence, or amino acid sequences, of Vα and/or Vβ TCR polypeptides present in the pretreatment and posttreatment samples may be determined. Because Vβ TCR polypeptide sequences generally exhibit more variability between TCRs than Vα TCR polypeptides, sequence analysis at this stage can be performed on only the amino acid sequence, or encoding nucleic acids, of Vβ TCR polypeptides (including fragments thereof such as the CDR3 of the Vβ TCR) in the pretreatment and posttreatment samples. The TCR alpha and/or beta sequences can then be compared to determine which were present in T cells present in diseased tissue prior to IL-10 agent therapy, and of these sequences, which were increased in frequency following IL-10 agent therapy. The TCR sequences that increase in frequency following IL-10 agent therapy above a selected background level are identified as associated with a TCR specific for an antigen of the diseased tissue (e.g., tumor antigen-specific, viral antigen specific), and represent TCRs present in T cell clones expanded by IL-10 agent therapy.

Amino acid sequences, encoding nucleic acid sequences, as well as constructs containing such encoding nucleic acids, of Vα and/or Vβ TCR polypeptides of disease antigen-specific TCRs identified (e.g., of Vα and/or Vβ TCR polypeptides, including Vα/Vβ polypeptide pairs of a TCR) are of particular interest for inclusion in a library of nucleic acids and/or clones, as well as in a database of nucleic acid sequence and/or amino acid sequence information. Similarly, the present disclosure provides for the construction of a database of nucleic acid and/or amino acid sequence information for at least Vβ polypeptides, and can optionally include Vα polypeptide sequence information, as well as sequence information of Vα/Vβ polypeptide pairs of T cells present in pretreatment samples.

Disease antigen binding specificity can be analyzed by assessing specific binding to pretreatment disease tissue of the patient, e.g., by testing specific binding of a CD8+ T cell genetically modified to express a recombinant TCR (e.g., CAR-T) comprising a TCR alpha/beta pair identified by being upregulated or induced in response to IL-10 agent therapy. Disease antigens bound by such recombinant TCRs, and/or T cell epitopes of such antigens, can be identified according to methods known in the art.

Where the antigen is a known antigen, the present methods can be used to identify, for example, new T cell epitopes and/or new alpha/beta TCR polypeptide pairs that bind an epitope of a known antigen. In some cases, CD8+ T cells, e.g., isolated CD8+ T cells that are specific to a known antigen may be contacted with the known antigen that is conjugated to a support, e.g., a magnetic bead, a column, etc., thereby separating cells specific to the known antigen from those that are not specific. In some cases, the CD8+ T cells, e.g., isolated CD8+ T cells that are specific to a known antigen may be contacted with the known antigen that is conjugated to a fluorescent moiety, and the cells sorted based on the fluorescence level, e.g., by FACS, to isolate the antigen-specific T cells. Suitable methods are described in, e.g., US 2006013470, which is incorporated herein by reference. Any suitable known antigen may be used. In some cases, where the patient to whom the IL-10 agent therapy has been administered has a cancer, the antigen to which the induced CD8+ T-cells are directed is a known tumor-associated antigen. A wide variety of tumor associated antigens are known in the art including, without limitation, CBX2, PLAC1, CLDN6, SPANX, MAGEA3, TPTE, ACTL8, ANKRD30A, CDKN2A, MAD2L1, CTAG1B, MAGEA4, MAGEA5, SUNC1, MAGEA10, LRRN1, MAGEA9, WT1, carcinoembryonic antigen (CEA), alphafetoprotein (AFP), CA19-9, CA125, PSA, CA72-4, SCC, MK-1, MUC-1, p53, HER2, G250, gp-100, melanoma-associated antigen (MAGE)-1, -2 and -3, BAGE, SART, MART, MYCN, BCR-ABL, TRP, LAGE, GAGE, tyrosinase, epithelial tumor antigen (ETA), Her-2/Neu, serum prostate specific antigen (PSA), and NY-ESO1. In some embodiments, where the patient to whom the IL-10 agent therapy has been administered has an infectious disease, the known antigen is a viral antigen such as CMV pp65, HIV gp120, etc., or any other known antigenic peptide from an intracellular pathogen, as described above.

Libraries.

Also provided herein is a library of nucleic acid constructs, e.g., vectors, wherein the library represents a plurality of antigen-specific TCR α and β chain pair sequences, or at least one or more of the variable regions thereof, obtained using a method as described herein. In some cases, each construct of the library may contain an antigen-specific TCR α and β chain pair sequence, or at least on or more of the variable regions thereof, e.g., as a multicistronic construct, or as a CAR.

Production of genetically modified T cells. The patient-specific sequences and/or consensus sequences of paired alpha and beta chains of the TCR expressed on the surface of CD8+ T cells, e.g., isolated CD8+ T cells find use in generating a population of transgenic CD8+ T cells that target disease-specific antigens and provide therapeutic effects when administered to an individual (including but not limited to the patient from whom the induced CD8+ T-cells were isolated) in need, as further described below.

Aspects of the present method may include cloning nucleic acids containing nucleotide sequences that encode each of the disease antigen-specific Vα and Vβ TCR pairs into one or more vectors configured to express a TCR, or a TCR-like receptor (such as a chimeric antigen receptor (CAR), as described further below) in a T cell. Cloning the nucleic acids may be done using any suitable method. The vector may be any suitable vector for cloning and/or expressing a TCR subunit, or TCR-like receptor, e.g., CAR, in a T cell. In some embodiments, the vector is an expression vector. The expression vector may be introduced into the host cells by any of a number of known gene transfer systems (e.g., natural competence, chemically mediated transformation, protoplast transformation, electroporation, biolistic transformation, transfection, or conjugation). The gene transfer system selected depends upon the host cells and vector systems used. In some cases, the vector is a viral vector, e.g., a retroviral or lentiviral vector (see, e.g., Jones et al., *Hum Gene Ther.* 2009 June; 20(6):630-40).

In some cases, a single vector is configured to express a gene product containing both the α and β chains, or at least the variable regions thereof, of a TCR, e.g., as full length TCRs, or as a chimeric antigen receptor that contains a single chain T cell receptor (scTv), as described further below.

Genetically Modified T Cells, Production of Same, and Methods of Use in Therapy

The present disclosure contemplates de novo generation, identification, expansion, production and use of genetically modified T cells which express a recombinant, disease antigen-specific TCR, as well as methods of use in therapy.

Production of Genetically Modified T Cells

The present disclosure provides genetically modified T cells, said T cells modified to express a recombinant T cell receptor (TCR), said TCR comprising one, two, and/or three complementarity determining regions (CDRs) of a variable alpha (Vα) T cell receptor (TCR) polypeptide and one, two, and/or three CDRs of a variable beta (Vβ) TCR polypeptide of a Vα/Vβ TCR pair, said Vα/Vβ TCR pair derived from a disease antigen-specific TCR of a PD1+, CD8+ peripheral T cell induced in a mammal in response to the administration of an IL-10 agent. In one embodiment, the TCR expressed on the genetically modified T-cell may comprise the full-length Vα and Vβ polypeptides of a Vβ TCR pair derived from a disease antigen-specific TCR of a CD8+ peripheral T cell induced in a mammal in response to the administration of an IL-10 agent.

In one embodiment, the genetically modified T cell is a chimeric antigen receptor T cell. Chimeric antigen receptor T cells (CARs; also known as artificial T cell receptors, chimeric T cell receptors, and chimeric immunoreceptors) represent an emerging therapy for cancer (e.g., treatment of B and T cell lymphomas) and other malignancies. CAR T cells can comprise autologous (patient-derived) or syngeneic donor memory CD8+ T cells (e.g., CD45RO+, CD8+ T cells) modified to express a recombinant T cell receptor specific for a known disease antigen (e.g., an antigen present on, for example, a tumor of interest). It should be noted that where syngeneic donor T cells are used, the T cells may be further genetically modified to disrupt expression (e.g., knock out) of the endogenous TCR. Other types of T cells contemplated herein include naïve T cells, central memory T cells, effector memory T cells or combination thereof. While the present disclosure is generally described in the context of using CAR T cell therapy for the treatment of cancer, it is to be understood that such therapy is not so limited. CAR T cell therapy can find use in treating any disease amenable to CD8+ T cell therapy, e.g., viral infections.

CAR T cell therapy can involve use of adoptive cell transfer (ACT). ACT, which utilizes a patient's own cultured T cells, has shown promise as a patient-specific cancer therapy (Snook and Waldman (2013) Discov Med 15(81): 120-25). The use of genetic engineering approaches to insert antigen-targeted receptors of defined specificity into T cells has greatly extended the potential capabilities of ACT. In most instances, these engineered chimeric antigen receptors are used to graft the specificity of a monoclonal antibody onto a T cell.

The initiation of CART cell therapy comprises the removal of T cells from a patient or from a donor having sufficient MHC compatibility with the patient. The T cells are then genetically engineered to express CARs directed towards antigens specific for a known cancer (e.g., a tumor). Following amplification ex vivo to a sufficient number, the autologous cells are infused back into the patient, resulting in the antigen-specific destruction of the cancer.

CARs are a type of antigen-targeted receptor composed of intracellular T-cell signaling domains generally fused to extracellular antigen-binding moieties, most commonly single-chain variable fragments (scFvs) from monoclonal antibodies. CARs directly recognize cell surface antigens, independent of MHC-mediated presentation, permitting the use of a single receptor construct specific for any given antigen in multiple patients.

Chimeric antigen receptors generally comprise several primary components, some of which are described hereafter. Chimeric antigen receptors in which antigen binding specificity is provided by complementarity determining regions (CDRs) of a variable alpha (Vα) T cell receptor (TCR) polypeptide and CDRs of a variable beta (Vβ) TCR polypeptide of a Vα/Vβ TCR pair are referred to herein as CAR-T, and genetically modified T cells comprising such CAR-T constructs as CAR-T T cells. The antigen binding portion of such CAR-T constructs may be referred to herein as a single chain T cell receptor, or "scTv".

As used herein, the phrase "antigen-specific targeting region" (ASTR) refers to the region that directs the CAR to specific antigens. The targeting regions of the CAR are extracellular. In particular embodiments of the present disclosure, the CARs comprise at least two targeting regions which target at least two different antigens. In further embodiments, the CARs comprise three or more targeting regions which target at least three or more different antigens.

In the context of the present disclosure, the ASTR of the CAR-T comprises one, two or three CDRs, the CDR having a sequence corresponding to a CDR of a variable alpha (Vα) T cell receptor (TCR) polypeptide and one, two or three CDRs, the CDR having a sequence corresponding to a CDR of a variable beta (Vβ) TCR polypeptide of a Vβ TCR pair of a disease antigen-specific TCR of a CD8+ peripheral T cell induced in a mammal in response to the administration of an IL-10 agent. In one embodiment, the ASTR of the of the CAR-T comprises the full-length Vα and Vβ polypeptides of a Vβ TCR pair derived from a disease antigen-specific TCR of a CD8+ peripheral T cell induced in a mammal in response to the administration of an IL-10 agent. In another embodiment, the ASTR of the of the CAR-T comprises Vα and Vβ polypeptides having 90% or more sequence homology to a Vβ TCR pair derived from a disease antigen-specific TCR of a CD8+ peripheral T cell induced in a mammal in response to the administration of an IL-10 agent.

In general, the ASTR comprises a single chain polypeptide comprising a Vβ polypeptide operably linked to a Vα polypeptide (e.g., through a peptide linker) to provide an ASTR of a single chain TCR (scTv). For example, an ASTR of a scTv may have the general structure, from N- to C-terminus, Vβ polypeptide-linker-Vα polypeptide. The C-terminus of the Vα polypeptide of the ASTR of the scTv is operably fused to the additional components of the scTV, e.g., from N- to C-terminus, an extracellular spacer domain, a transmembrane domain, and an intracellular signaling domain, examples of each of which are provided below. Methods for producing scTV are described in the art, see, e.g., US 2012/0252742. The present disclosure also contemplates soluble polypeptides comprising an ASTR of an scTv ("soluble scTv"). In such instances, these polypeptides include a polypeptide to facilitate solubility, e.g., human serum albumin fused to N-terminus of the Vβ polypeptide of ASTR of the scTv.

As used herein, the term "extracellular spacer domain" (ESD) refer to the hydrophilic region of the CAR between the antigen-specific targeting region and the transmembrane domain. The present disclosure contemplates embodiments wherein the CAR-Ts comprise an ESD, examples of which include hinge regions of CD8 and other domains as described in, for example, US 2012/0252742; artificial spacer sequences, including Gly3 or CH1 and CH3 domains of IgGs (such as human IgG4); or combinations of the foregoing. One of ordinary skill in the art is aware of other ESDs, which are contemplated herein.

As used herein, the term "transmembrane domain" (TMD) refers to the region of the CAR which traverses the plasma membrane. In some embodiments, the transmembrane region is a transmembrane protein (e.g., a Type I transmembrane protein), an artificial hydrophobic sequence, or a combination thereof. The skilled artisan is aware of other transmembrane domains which may be used in conjunction with the teachings of the present disclosure.

As used herein, the terms "intracellular signaling domain" (ISD) and "cytoplasmic domain" refer to the portion of the CAR which transduces the effector function signal and directs the cell to perform its specialized function. Examples of ISDs include the zeta chain of the T-cell receptor complex or any of its homologs (e.g., eta. chain, FcεR1γ and δ chains, MB1 (Igα) chain, B29 (Igβ) chain, etc.), human CD3 zeta chain, CD3 polypeptides (δ, Δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28. The skilled artisan is aware of other ISDs that may be used in conjunction with the teachings of the present disclosure.

The term "co-stimulatory domain" (CSD) refers to the portion of the CAR which enhances the proliferation, survival or development of memory cells. As indicated elsewhere herein, the CARs of the present disclosure may comprise one or more co-stimulatory domains. In some embodiments of the present disclosure, the CSD comprises one or more of members of the TNFR superfamily, CD28, CD137 (4-1BB), CD134 (OX40), Dap10, CD27, CD2, CD5, ICAM-1, LFA-1 (CD11a/CD18), Lck, TNFR-I, TNFR-II, Fas, CD30, CD40 or combinations thereof. The ordinarily skilled artisan is aware of other co-stimulatory domains that may be used in conjunction with the teachings of the present disclosure.

As used in conjunction with the CAR-T T cell technology described herein, the terms "linker", "linker domain" and "linker region" refer to an oligo- or polypeptide region from about 1 to 100 amino acids in length, which links together any of the domains/regions of the CAR of the disclosure. Linkers may be composed of flexible residues like glycine and serine so that the adjacent protein domains are free to move relative to one another. Certain embodiments comprise the use of linkers of longer length when it is desirable to ensure that two adjacent domains do not sterically interfere with each another. In some embodiments, the linkers are non-cleavable, while in others they are cleavable (e.g., 2A linkers (for example T2A)), 2A-like linkers or functional equivalents thereof, and combinations of the foregoing. Embodiments of the present disclosure are contemplated wherein the linkers include the picornaviral 2A-like linker, CHYSEL sequences of porcine teschovirus (P2A), Thosea asigna virus (T2A), or combinations, variants and functional equivalents thereof. In still further embodiments, the linker sequences comprise Asp-Val/Ile-Glu-X-Asn-Pro-Gly$^{(2A)}$-pro$^{(2B)}$ motif, which results in cleavage between the 2A glycine and the 2B proline. Other linkers will be readily apparent to the skilled artisan and are contemplated for use with the teachings of the present disclosure.

Methods of Use of Genetically Modified T Cells in Therapy

The genetically modified T cells (e.g., CAR-T T cells) described are useful either alone or conjunction with other therapeutic agents in the treatment of diseases amendment to CD8+ cell therapy. In general, a genetically modified T cell(s) (e.g., CAR-T T cell) is selected according to the disease to be treated.

The methods of the present disclosure contemplate administering one or more selected genetically modified CD8+ T cells to a mammalian subject suffering from a disease amenable to treatment with CD8+ cell therapy.

In one embodiment, the genetically modified CD8+ T cells administered mammalian subject suffering from a disease amenable to treatment with CD8+ cell therapy are a population of genetically modified CD8+ T cells which express the same recombinant TCR. In another embodiment, the genetically modified CD8+ T cells which are administered to a mammalian subject suffering from a disease amenable to treatment with CD8+ cell therapy are heterogeneous for the disease antigen-specific TCR expressed on the cell surface. In this latter approach, the different Vα/Vβ TCR pairs of genetically modified CD8+ T cells in the population may be selected as to bind to the same disease antigen (e.g., different epitopes of the same antigen) or to different disease antigens.

Treatments comprising administration of genetically modified T cells (e.g., CAR-T T cells), optionally in combination therapy, contemplated by the present disclosure include treatment or prevention of a proliferative disease, disorder or condition, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present disclosure also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The disclosure contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

The present disclosure also contemplates use of the genetically modified T cell therapy (such as the CAR-T cell therapy) as described herein, optionally in combination therapy, for treating or preventing a disease caused by a viral infection. Examples viral agents include single-stranded DNA (ssDNA), double-stranded DNA (dsDNA) and RNA viruses. In some embodiments, the virus is a hepadnavirus, flavivirus, retrovirus, or herpes virus. In some cases, the disease may be caused by, without limitation, hepatitis type A, hepatitis type B (HBV), hepatitis type C (HCV), influenza, varicella-zoster virus (VZV), adenovirus, Epstein-Barr virus (EBV), herpes simplex type I (HSV-I), herpes simplex type II (HSV-II), rhinovirus, echovirus, rotavirus, respiratory syncytial virus, human papilloma virus (HPV), papova virus, cytomegalovirus (CMV), echinovirus, arbovirus, huntavirus, coxsachie virus, mumps virus, measles virus, rubella virus, polio virus, human immunodeficiency virus type I (HIV-I), and human immunodeficiency virus type II (HIV-II), human T lymphotropic viruses (HTLV-1 and HTLV-2), coronavirus, poliomyelitis virus, human herpes virus 6 (HHV-6), etc.

Combination Therapies

The present disclosure also contemplates both genetically modified T cell monotherapy as well as combination therapy. For example, genetically modified T cells of the present invention may be administered to a mammalian subject alone or combination with one or more active agents (e.g., chemotherapeutic agents) or other prophylactic or therapeutic non-pharmacological modalities (e.g., localized radiation therapy or total body radiation therapy), may be used in a combination therapy with genetically modified T cells. By way of example, the present disclosure contemplates treatment regimens wherein a radiation phase is preceded or followed by treatment with one or more additional therapies (e.g., CAR-T T cell therapy and, optionally, administration of an IL-10 agent) or agents as described herein. In some embodiments, the present disclosure further contemplates the use of CAR-T T cell therapy and an IL-10 agent (e.g., PEG-IL-10) in combination with bone marrow transplantation, peripheral blood stem cell transplantation, or other types of transplantation therapy.

As used herein, "combination therapy" is meant to include therapies that can be administered or introduced separately, for example, formulated separately for separate administration (e.g., as may be provided in a kit), and therapies that can be administered or introduced together. In certain embodiments, the genetically modified T cell (e.g., CAR-T T cell), and/or the other agent(s) are administered or applied sequentially, e.g., where one agent is administered prior to one or more other agents. In other embodiments, the genetically modified T cell (e.g., CAR-T T cell) and the other agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

The genetically modified T cells (e.g., CAR-T T cell), of the present disclosure may be used in combination with at least one other active agent in any manner appropriate under the circumstances. In one embodiment, treatment with the genetically modified T cell (e.g., CAR-T T cell), optionally with an IL-10 agent and/or other agent(s), is maintained over a period of time. In another embodiment, treatment with the at least one other agent(s) is reduced or discontinued (e.g., when the subject is stable), while treatment with a genetically modified T cell (e.g., CAR-T T cell), optionally with an IL-10 agent (e.g., PEG-IL-10), is maintained at a constant dosing regimen. In a further embodiment, treatment with the other agent(s) is reduced or discontinued (e.g., when the subject is stable), while treatment with a genetically modified T cell (e.g., CAR-T T cell), and optionally, an IL-10 agent, is reduced (e.g., lower dose, less frequent dosing or shorter treatment regimen). In yet another embodiment, treatment with the other agent(s) is reduced or discontinued (e.g., when the subject is stable), and treatment with the a genetically modified T cell (e.g., CAR-T T cell), optionally with IL-10 agent, is increased (e.g., higher dose, more frequent dosing or longer treatment regimen). In yet another embodiment, treatment with the other agent(s) is maintained and treatment with a genetically modified T cell (e.g., CAR-T T cell), and optionally an IL-10 agent, is reduced or discontinued (e.g., lower dose, less frequent dosing or shorter treatment regimen). In yet another embodiment, treatment with the other agent(s) and treatment with an IL-10 agent of the present disclosure (e.g., PEG-IL-10) are reduced or discontinued (e.g., lower dose, less frequent dosing or shorter treatment regimen), and treatment with a genetically modified T cell (e.g., CAR-T T cell) is maintained.

In conjunction with a genetically modified T cell therapy (such as a CAR-T T cell therapy) as described herein, the present disclosure provides methods for treating and/or preventing a proliferative condition, cancer, tumor, or precancerous disease, disorder or condition with a genetically modified T cell (e.g., CAR-T T cell) having a TCR specific for an antigen of the proliferative condition, cancer, tumor, or precancerous disease, disorder or condition, and optionally an IL-10 agent (e.g., PEG-IL-10) and, optionally, at least one additional therapeutic or prophylactic agent(s) or diagnostic agent exhibiting a desired activity. Some embodiments of the present disclosure contemplate the use of traditional chemotherapeutic agents (e.g., alkylating agents, nitrogen mustards, nitrosureas, antibiotics, anti-metabolites, folic acid analogs, purine analogs, pyrimidine analogs, antihormonal agents and taxoids). Other embodiments of the present disclosure contemplate methods for tumor suppression or tumor growth comprising administration of an IL-10 agent described herein in combination with a signal transduction inhibitor (e.g., GLEEVEC or HERCEPTIN) or an immunomodulator to achieve additive or synergistic suppression of tumor growth.

In conjunction with the genetically modified T cell therapy (such as the CAR-T T cell therapy) as CAR-T T cell therapy described herein, the present disclosure also provides methods for treating viral infections by administering a genetically modified T cell (e.g., CAR-T T cell) having a TCR specific for an antigen of the infecting virus. Such therapies may include administration of an IL-10 agent (e.g., PEG-IL-10), and/or an antiviral agent.

Pharmaceutical Compositions

When a therapeutic agent, such as a genetically modified T cell (e.g., CAR-T T cell) or an IL-10 agent, is administered to a subject, the present disclosure contemplates the use of any form of compositions suitable for administration to the subject. In general, such compositions are "pharmaceutical compositions" comprising the therapeutic agent (e.g., genetically modified T cell (e.g., CAR-T T cell) or IL-10) and one or more pharmaceutically acceptable or physiologically acceptable diluents, carriers or excipients. The pharmaceutical compositions can be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions can be used in combination with other therapeutically active agents or compounds as described herein in order to treat or prevent the diseases, disorders and conditions as contemplated by the present disclosure.

The pharmaceutical compositions typically comprise a therapeutically effective amount of a therapeutic agent contemplated by the present disclosure (e.g., genetically modified T cell (e.g., CAR-T T cell) or an IL-10 agent) and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle can be a physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it can be stored in sterile container, such as a vial or a syringe. In some embodiments, and where appropriate, the pharmaceutical composition is provided in a single-use container (e.g., a single-use vial, ampoule, syringe, or auto-injector (similar to, e.g., an EpiPen®)), whereas a multi-use container (e.g., a multi-use vial) is provided in other embodiments. For IL-10 agents, any drug delivery apparatus can be used to deliver IL-10, including implants (e.g., implantable pumps) and catheter systems, slow injection pumps and devices, all of which are well known to the skilled artisan. Depot injections, which are generally administered subcutaneously or intramuscularly, can also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions can be in the form of a sterile injectable aqueous or oleagenous suspension. This suspension can be formulated according to the known art using those suitable dispersing or wetting agents and suspending agents mentioned herein. The sterile injectable preparation can also be a sterile injectable solution or suspension in a non-toxic parenterally-acceptable diluent or solvent, for example, as a solution in 1,3-butane diol. Acceptable diluents, solvents and dispersion media that can be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil can be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

Formulations can also include carriers to protect the composition against rapid degradation or elimination from the body, such as a controlled release formulation, including implants, liposomes, hydrogels, prodrugs and microencapsulated delivery systems.

Kits

The present disclosure also contemplates kits comprising a genetically modified T cell (e.g., CAR-T T cell) having a TCR specific for an antigen of target disease, optionally with an IL-10 agent (e.g., PEG-IL-10), and pharmaceutical compositions thereof. The kits are generally in the form of a physical structure housing various components, as described below, and can be utilized, for example, in practicing the methods described above.

A kit can include a genetically modified T cell (e.g., CAR-T T cell), and/or construct(s) encoding a desired disease antigen-specific TCR for use in production of genetically modified T cells, as disclosed herein (provided in, e.g., a sterile container), which can be in the form of a pharmaceutical composition suitable for administration to a subject.

Where provided, the IL-10 agent can be provided in a form that is ready for use or in a form requiring, for example, reconstitution or dilution prior to administration. When the IL-10 agent is in a form that needs to be reconstituted by a user, the kit can also include buffers, pharmaceutically acceptable excipients, and the like, packaged with or separately from the IL-10 agent. A kit can also contain both the IL-10 agent and/or components of the specific CAR-T T cell therapy to be used; the kit can contain the several agents separately or they can already be combined in the kit. A kit of the present disclosure can be designed for conditions necessary to properly maintain the components housed therein (e.g., refrigeration or freezing).

A kit can contain a label or packaging insert including identifying information for the components therein and instructions for their use (e.g., dosing parameters, clinical pharmacology of the active ingredient(s), including mechanism(s) of action, pharmacokinetics and pharmacodynamics, adverse effects, contraindications, etc.). Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via an internet site, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: s or sec=second(s); min=minute(s); h or hr=hour(s); aa=amino acid(s); bp=base pair(s); kb=kilobase(s); nt=nucleotide(s); ng=nanogram; μg=microgram; mg=milligram; g=gram; kg=kilogram; dl or dL=deciliter; μl or μL=microliter; ml or mL=milliliter; l or L=liter; nM=nanomolar; μM=micromolar; mM=millimolar; M=molar; kDa=kilodalton; i.m.=intramuscular(ly); i.p.=intraperitoneal(ly); SC or SQ=subcutaneous(ly); HPLC=high performance liquid chromatography; BW=body weight; U=unit; ns=not statistically significant; PMA=Phorbol 12-myristate 13-acetate; PBS=phosphate-buffered saline; DMEM=Dulbeco's Modification of Eagle's Medium; PBMCs=primary peripheral blood mononuclear cells; FBS=fetal bovine serum; FCS=fetal calf serum; HEPES=4-(2-hydroxyethyl)-1-piperazineethanesulfonic acid; LPS=lipopolysaccharide; RPMI=Roswell Park Memorial Institute medium; APC=antigen presenting cells; FACS=fluorescence-activated cell sorting.

Materials and Methods.

The following general materials and methods were used, where indicated, or may be used in the Examples below:

Molecular Biology Procedures.

Standard methods in molecular biology are described in the scientific literature (see, e.g., Sambrook and Russell (2001) Molecular Cloning, $3^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.). Further discussion of antibodies appears elsewhere herein.

Software.

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

Pegylation.

Pegylated IL-10 as described herein may be synthesized by any means known to the skilled artisan. Exemplary synthetic schemes for producing mono-PEG-IL-10 and a mix of mono-/di-PEG-IL-10 have been described (see, e.g., U.S. Pat. No. 7,052,686; US Pat. Publn. No. 2011/0250163; WO 2010/077853). Particular embodiments of the present disclosure comprise a mix of selectively pegylated mono- and di-PEG-IL-10. In addition to leveraging her own skills in the production and use of PEGs (and other drug delivery technologies) suitable in the practice of the present disclosure, the skilled artisan is familiar with many commercial suppliers of PEG-related technologies (e.g., NOF America Corp (Irvine, Calif.) and Parchem (New Rochelle, N.Y.)).

Animals.

Various mice and other animal strains known to the skilled artisan can be used in conjunction with the teachings of the present disclosure. For example, immunocompetent Balb/C or B-cell-deficient Balb/C mice can be obtained from The Jackson Lab., Bar Harbor, Me. and used in accordance with standard procedures (see, e.g., Martin et al (2001) Infect. Immun., 69(11):7067-73 and Compton et al. (2004) Comp. Med. 54(6):681-89).

IL-10 Concentrations.

Serum IL-10 concentration levels and exposure levels can be determined by standard methods used in the art. For example, when the experimental subject is a mouse, a serum exposure level assay can be performed by collecting whole blood (~50 μL/mouse) from mouse tail snips into plain capillary tubes, separating serum and blood cells by centrifugation, and determining IL-10 exposure levels by standard ELISA kits and techniques.

FACS Analysis.

Numerous protocols, materials and reagents for FACS analysis are commercially available and may be used in conjunction with the teachings herein (e.g., Becton-Dickinson, Franklin Lakes, N.J.; Cell Signaling Technologies, Danford, Mass.; Abcam, Cambridge, Mass.; Affymetrix, Santa Clara, Calif.). Both direct flow cytometry (i.e., using a conjugated primary antibody) and indirect flow cytometry (i.e., using a primary antibody and conjugated secondary antibody) may be used. An exemplary direct flow protocol is as follows: Wash harvested cells and adjust cell suspension to a concentration of $1-5 \times 10^6$ cells/mL in ice-cold PBS, 10% FCS, 1% sodium azide. Cells may be stained in polystyrene round bottom $12 \times 75$ mm$^2$ Falcon tubes. Cells may be centrifuged sufficiently so the supernatant fluid may be removed with little loss of cells, but not to the extent that the cells are difficult to resuspend. The primary labeled antibody may be added (0.1-10 μg/mL), and dilutions, if necessary, may be made in 3% BSA/PBS. After incubation for at least 30 min at 4° C., cells may be washed 3× by centrifugation at 400 g for 5 min and then may be resuspended in 0.5-1 mL of ice-cold PBS, 10% FCS, 1% sodium azide. Cells may be maintained in the dark on ice until analysis (preferably within the same day). Cells may also be fixed, using standard methodologies, to preserve them for several days; fixation for different antigens may require antigen-specific optimization.

The assays described hereafter are representative, and not exclusionary.

Recombinant Murine IL-10 (rMuIL-10), Pegylated-rMuIL-10 (PEG-rMuIL-10), Pegylated rHuIL-10 (PEG-rHuIL-10).

Pegylated IL-10 used in the examples below was a mixture of mono-/di-PEG-IL-10 mix as described in the patent literature (e.g., U.S. Pat. No. 8,691,205). Two examples of synthetic schemes for production of a mono/di-PEG-IL-10 mixture are provided below:

Pegylated IL-10 Synthesis Scheme No. 1.

IL-10 (e.g., murine or human) is dialyzed against 50 mM sodium phosphate, 100 mM sodium chloride pH ranges 5-7.4. A 1:1-1:7 molar ratio of 5 kDa PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours. The pH of the pegylation reaction is adjusted to 6.3, and 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-PEG IL-10 are the largest products of the reaction, with the concentration of each at ~50% at termination. The reaction may be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

Pegylated IL-10 Synthesis Scheme No. 2.

IL-10 (e.g., murine or human) is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12 kDa (Delmar Scientific Laboratories, Maywood, Ill.) and one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate, and the reaction solution is mildly agitated. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C. PEG-IL-10 was formulated at 0.75-1.0 mg/mL in 10 mM HEPES, pH 6.5, 100 mM NaCl containing 0.05% MSA.

The mixture of mono- and di-pegylated-rHuIL-10 used herein may be referred to as AM0010, and was synthesized using a 5 kDa PEG and a PPA linker, and can be synthesized as set out in scheme 1 above.

Isolation and IL-10 Treatment of Murine CD8+ T Cells:

Murine CD8+ T cells were magnetically isolated (Miltenyi, Auburn, Calif.) from OT1 mice (C56B1/6-Tg(TcraTcrb) 1100Mjb/J, The Jackson Laboratory, Bar Harbor, Me.) and cultured in 100-1000 IU/mL rMuIL-2, (R&D Systems, Minneapolis, Minn.) for 7-10 days. OT1 T cells were re-stimulated with autologous myeloid cells activated with 1 μg/mL LPS, (Sigma Aldrich, St. Louis, Mo.) for 3 days and exogenously pulsed with SIINFEKL (SEQ ID NO: 35) peptide (InvivoGen, San Diego, Calif.). Three days after re-stimulation, cells were exposed to stated concentrations of rMuIL-10 for 5 days. Cells were then washed and exposed to PDV6 cells pulsed with SIINFEKL (SEQ ID NO: 35) peptide (Merck Research Labs, Palo Alto, Calif.). Percent cell lysis was determined for CellTiter Glo, (Promega, Madison, Wis.) according to manufacturer's instructions.

Isolation and IL-10 Treatment of Human CD8+ T Cells:

Human CD8+ T cells were magnetically isolated (Miltenyi) from normal, "healthy" human melanoma tumor biopsies. Tumor cells were cultured in 6-well plates, (Nunclon, Thermo Fisher Scientific, Waltham, Mass.) and T cells were cultured separately in 24-well plates, (Nunclon). CD8+ T cells were cultured in complete RPMI, (Hyclone, GE Healthcare Life Sciences, Logan, Utah) supplemented with 100-1000 IU/mL IL-2 (Chiron, Emeryville, Calif.) and re-fed every 5-7 days. T cells were re-stimulated with heat-lysed tumor cell antigens that were exogenously added to TT cells (ATCC CRL-1803, Manassas, Va.) to act as antigen presenting cells every 10-12 days. Three days after re-stimulation, CD8+ T cells were washed and exposed to stated concentrations of rHuIL-10 for 5 days. Cells were washed and added to labeled cognate tumor cells Cr51 (Perkin Elmer, Waltham, Mass.), A375 tumor cells (ATCC CRL-1619, Manassas, Va.) or K562 cells (ATCC CCL-243) at the effector to target stated and a standard 4-hour chromium release assay was performed.

ELISPOT:

Murine CD8+ T cells were isolated from CT26, (ATCC CRL-2638) tumor bearing mice after stated dosing with PEG-rMuIL-10 (Merck Research Labs) by magnetic bead separation (Miltenyi). Cells were washed and plated at 1000-5000 cells per ELISPOT (R&D systems, Minneapolis, Minn.) in triplicate. Wells contained nothing, 1 µg/mL anti-CD3 (eBioscience, San Diego, Calif.), 100-500 CT26, or 100-500 4T1 (ATCC CRL-2539) pre-exposed for 1 hour to 10 ng/mL IFNγ (R&D Systems, Minneapolis, Minn.). Plates were incubated at 37° C. with 5% $CO_2$ for 24 hours and developed according to manufacturer's instructions. Plate images were captured using a CTL (Shaker Heights, Ohio) Immunospot analyzer, and spots were quantified using ImmunoSpot ELISPOT Analysis Software.

qPCR:

RNA is extracted and cDNA is synthesized from the isolated CD8+ T cells using Qiagen's RNeasy Kit and $RT^2$ First Strand Kit, respectively, following the manufacturer's instructions. Quantitative PCR is performed on the cDNA template using the $RT^2$ SYBR Green qPCR Mastermix and primers from Qiagen according to the manufacturer's protocol. Ct values are normalized to the average Ct value of the housekeeping genes, GUSB and GAPDH.

CT26 Tumor Model:

Female C57BL/6J mice (Jackson Laboratory) mice, 4-to-6 weeks of age, were implanted with $1 \times 10^5$ CT26 cells (CRL-2638; ATCC) in a volume of 100 µL, subcutaneously, on the animal's right lower flank. Once palpable, growth of tumors was measured twice weekly. Tumor volume was calculated using the formula (width$^2$×length/2) where length is the longer dimension. When tumors reached an average of 75 mm$^3$ in volume, animals were stratified. Five mice/cohort were administered vehicle or pegylated recombinant IL-10 (Schering-Plough, Palo Alto, Calif.), subcutaneously, every day for 28 days. After 28 days of dosing, mice from each group were sacrificed for tissue and tumor analysis.

4T1 Tumor Model:

Female BALB/c (Jackson Laboratory) mice, 4-to-6 weeks of age, were implanted with $1 \times 10^4$ 4 T1 cells (CRL-2539; ATCC) in a volume of 100 µL, subcutaneously, on the animal's right lower flank. Once palpable, growth of tumors was measured twice weekly. Tumor volume was calculated using the formula (width$^2$×length/2) where length is the longer dimension. When tumors reached an average of 75 mm$^3$ in volume, animals were stratified. Five mice/cohort were administered vehicle or pegylated recombinant IL-10 (ARMO Biosciences, Redwood City, Calif.), subcutaneously, every day for 28 days. After 28 days of dosing, mice from each group were sacrificed for tissue and tumor analysis.

Isolation of Tumor Infiltrating Lymphocytes:

To isolate tumor infiltrating lymphocytes (TILs), tumors were minced with 5 mL of digest buffer (RPMI (Life Technologies), 10% Fetal Bovine Serum (Hyclone Thermo Fisher Scientific), 10 mM HEPES (Life Technologies), 2 mg/mL Collagenase Type I (Worthington Biochemical, Lakewood, N.J.), 30 U/mL DNaseI (Worthington Biochemical) and brought to a final volume of 35 mL with digest buffer. The tumor slurry was rotated at 37° C. for 45 minutes. The tumor slurry was then mechanically disrupted by forcing the material through a 70 micron cell strainer. Cells were washed with RPMI twice and then resuspended with 25 mL of HBSS (Life Technologies). Cell suspensions were underlayed with 15 mL Histopaque (Sigma-Aldrich, St. Louis, Mo.) and centrifuged at 1000 rpm for 30 minutes at room temperature with the brakes turned off. After centrifugation, the cell interface, containing TILs, was collected and washed twice with complete RPMI. CD8+ T cells were then isolated using MACS cell separation technology (Miltenyi Biotec) following the manufacturer's protocol. The isolated CD8+ T cells were treated with 1 µg/mL anti-CD3 and 1 µL GolgiPlug (BD Biosciences, San Jose, Calif.) per mL cells for 10 hours prior to antibody staining and flow cytometric analysis.

Activation Induced Cell Death Assay:

An exemplary activation induced cell death assay can be performed using the following protocol. Human primary peripheral blood mononuclear cells (PBMCs) were isolated according to standard protocol (see, e.g., Fuss et al. (2009) Current Protocols in Immunology, Unit 7.1, John Wiley, Inc., NY). CD45RO+CD8 T cells were isolated using Miltenyi Biotec's anti-CD45RO MACS beads and MACS cell separation technology according to the manufacture's protocol (Miltenyi Biotec). CD45RO is a marker of memory T cells. To activate cells, 1 mL of isolated cells (at a density of $3 \times 10^6$ cells/mL) were cultured in AIM V media for 3 days (Life Technologies) in a standard 24-well plate (BD; Franklin Lakes, N.J.) which was pre-coated with anti-CD3 and anti-CD28 antibodies (Affymetrix eBioscience, San Diego, Calif.). To pre-coat 24-well plates with anti-CD3 and anti-CD28 antibodies, 300 µL of carbonate buffer (0.1 M $NaHCO_3$ (Sigma-Aldrich), 0.5 M NaCl (Sigma-Aldrich), pH 8.3) containing 10 µg/mL anti-CD3 and 2 µg/mL anti-CD28 antibodies were incubated in each well for 2 hours at 37° C. and then each well was washed with AIM V media. Following the 3-day activation, cells were collected, counted, re-plated in 1 mL of AIM V media (at a density of $2 \times 10^6$ cells/mL) in a standard 24-well plate and treated with 100 ng/mL human pegylated IL-10 for 3 days. Next, the above-described activation and treatment with human pegylated IL-10 was repeated, after which viable cells were counted by Trypan Blue exclusion following the manufacturer's procedures (Life Technologies) or stained for flow cytometric analysis.

Flow Cytometry:

Isolated mouse tumor infiltrating CD8+ T cells were stained using the BD Cytofix/Cytoperm Plus Fixation/Permeabilization Kit (BD Biosciences) according to the manufacturer's protocol with anti-mouse IFNγ (BioLegend, San Diego, Calif., USA), CD8 (BioLegend), and PD1 (BioLegend) antibodies. For purposes of analysis in the experimental below, "PD1+ mid" cells generally express a level of cell surface PD1 that results in a mean channel fluorescent detection by flow cytometry of approximately 3000, while low PD1 expression ("PD1+low") is represented by a mean channel fluorescence detection of approximately 200 and "PD1+ high" expression is represented by a mean channel fluorescence detection of approximately 9000.

PEG-rHuIL-10 Therapy and Assessment of Tumor Response.

Human melanoma patients were treated with PEG-rHuIL-10 (AM0010) via subcutaneous daily self injection in the abdomen. The therapeutically active dose ranges from 5-20 µg/kg/day. Progressive disease (PD), stable disease (SD) and partial responses (PR) were assessed by computerized tomography (CT) scans. Patients were scanned at day 1, prior to administration of AM0010 and on 6-7 week intervals post initiation of dosing. Full body CT scans were used to assess tumor location and changes to tumor size. Target lesions were determined and the largest cross section of tumor mass was measured at each scan time point. Target lesions are assessed both by the radiologist and by the treating oncologist. Patients whose target lesions whose largest cross sectional aggregate volume, (measured in two dimensions) increased greater than 25% from one scan to the next conferred a progressive disease designation. Patients whose target lesions whose largest cross sectional aggregate volume, (measured in two dimensions) neither increased greater than 25% nor decreased greater than 50% from one scan to the next conferred a stable disease designation. Patients whose target lesions whose largest cross sectional aggregate volume, (measured in two dimensions) decreased greater than 50% from one scan to the next conferred a partial response disease designation.

Example 1: IL-10 Treatment of Murine CD8+ Cells Leads to Enhanced Function

The effects of IL-10 upon isolated murine CD8+ T cell function was assessed in vitro. Murine CD8+ T cells were isolated and treated with recombinant murine IL-10 (rMuIL-1) as described above or without rMuIL-10 as a control. T cell activation was assessed by qPCR analysis of gene expression of the cytotoxic markers Granzyme A, Granzyme B, Perforin and the cytokine IFNγ. T cell cytotoxicity was assessed by the ability of IL-10 treated, SIINFEKL (SEQ ID NO:35) -primed CD8+ T cells to lyse PDV6 cells pulsed with SIINFEKL (SEQ ID NO:35), as described above.

As shown in FIG. 1, Panel A, murine CD8+ cells stimulated in vitro with murine IL-10 exhibited enhanced expression of cytotoxic markers Granzyme A, Granzyme B, Perforin and the cytokine IFNγ. As shown in FIG. 1, Panel B, treatment of murine OT1 CD8+ T cells leads to enhanced cytotoxicity of SIINFEKL pulsed tumor cell targets.

Example 2: IL-10 Treatment of Human CD8+ Cells Isolated from Tumor Biopsies Leads to Enhanced Function Human CD8+ T cells were obtained from patient biopsies of melanoma tumors expanded in culture, re-stimulated with heat-lysed tumor cell antigens, and then cultured in the absence of IL-10 or in the presence of the stated concentrations of recombinant human IL-10 (rHuIL-10) as described above. T cell activation was assessed by qPCR analysis of gene expression of the cytotoxic markers Granzyme A, Granzyme B, Perforin and the cytokine IFNγ. T cell cytotoxicity was assessed by was assessed by the ability to lyse cognate melanoma tumor cells, A375 cells (a human amelanotic melanoma cell line), or K562 cells (a human myelogenous leukemia cell line).

As shown in FIG. 1, Panel C, in vitro rHuIL-10 treatment of stimulated intra-tumor derived human CD8+ T cells enhanced expression of Granzyme A, B, Perforin and IFNγ. In addition, as shown in rHuIL-10 treatment also lead enhanced cytotoxicity of cognate tumor cell targets. rHuIL-10 treatment of human CD8+ T cells did not result in marked increase of cytotoxicity against either A375 cells or K562 cells, indicating that the increased cytotoxicity is antigen-specific.

Example 3: Continued Treatment of Tumor Bearing Mice Leads to an Increase of Tumor Antigen Specific Intratumoral CD8+ T Cells CT26 tumor bearing mice were treated with 1 mg/kg PEG-rMuIL-10, or with vehicle as a control, daily for 6, 10 or 15 days, and CD8+ intratumoral T cells were isolated. ELISPOTs (R&D Systems) were generated by magnetic (Miltenyi) bead isolation of 1,000 CD8+ T cells from either PBMC or mechanically disrupted and enzyme digested CT26 (ATCC) tumors. CD8+ T cells were exposed for 24 hrs to no secondary stimulus, (w/o), 1 µg/mL soluble anti-CD3 (eBiosciences), 100 CT26 cells (ATCC, mouse squamous tumor) or 4T1 cells (ATCC, mouse breast tumor) (as negative control) tumor cells. Spots were quantified with ImmunoSpot Software.

Figure 2:
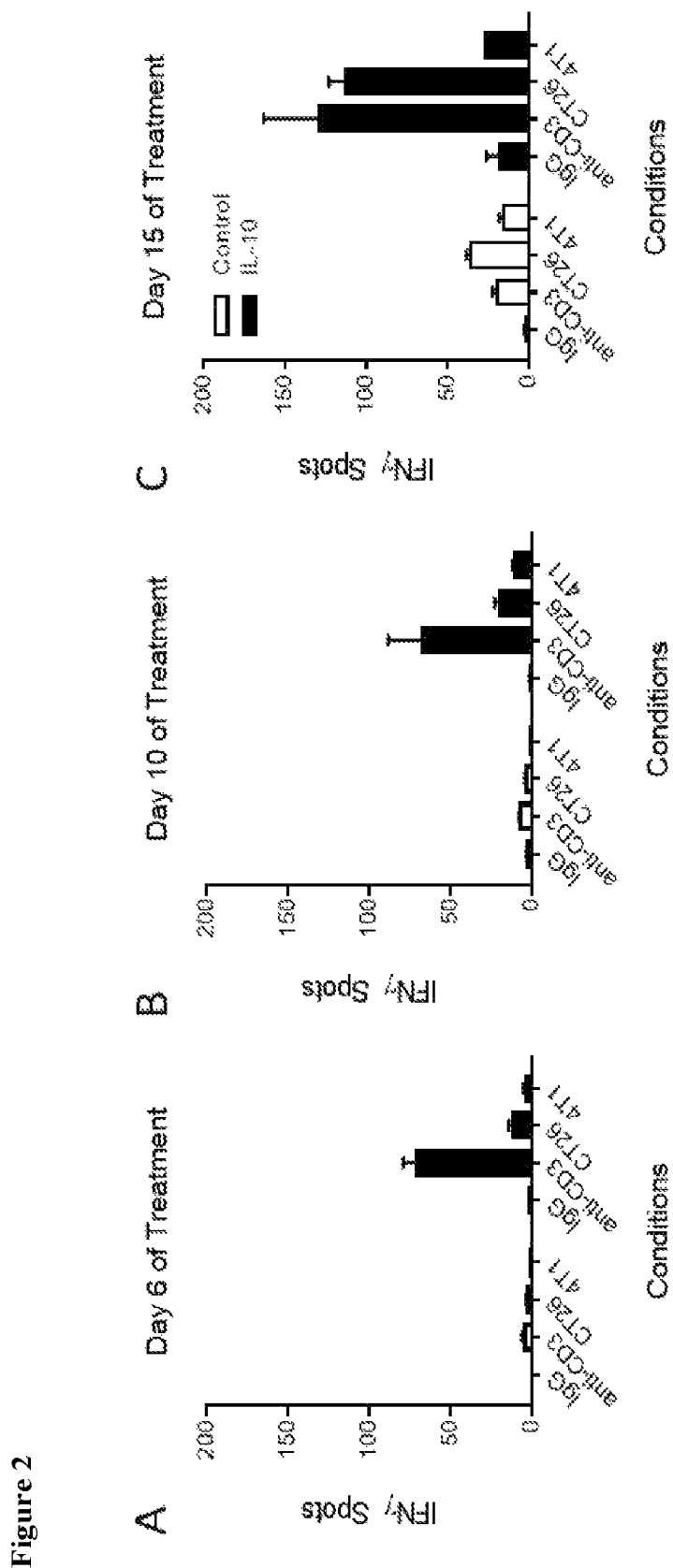
FIG. 2 illustrates the effects of treatment of tumor-bearing mice upon tumor antigen-specific intratumoral CD8+ T cells (also referred to as tumor infiltrating lymphocytes, or "TILs") for 6 days (Panel A), 10 days (Panel B), or 15 days (Panel C).

CD8+ T cells which secreted IFNγ when exposed to anti-CD3 are increased in the PEG-rMuIL-10 treated group (FIG. 2, Panel A). This indicates that PEG-rMuIL-10 treatment potentiates CD8+ T cell responses to TCR ligation. Similarly, CD8+ T cells which secreted IFNγ when exposed to cognate CT26 tumor cells also increase over time (FIG. 2, Panel B), such that by day 15 of treatment, all of the cells which secreted IFNγ upon TCR ligation with anti-CD3 also secreted IFNγ upon exposure to cognate tumor cells (FIG. 2, Panel C).

These results indicate that the CD8+ T cells that were activated by PEG-rMuIL-10 treatment and capable of secreting IFNγ are specific to tumor antigens. The observation that tumor antigen specific CD8+ T cells increase over time indicates that continual treatment with PEG-rIL-10 causes the gradual accumulation of tumor antigen specific CD8+ T cells whose alpha beta TCR sequences represent novel CART TCR constructs that are specific to solid tissue tumors.

Example 4: Continued IL-10 Treatment Modulates PD1 Expression on CD8+ T Cells

The effect of 15 days of treatment with PEG-rMuIL-10 as described in Example 3 on PD1 and IFNγ expression levels was assessed. PD1 is a marker of CD8+ T cell activation (Agata, et al., Int Immunol, 1996. 8(5): p. 765-72). Expression of PD1 is also associated with activation induced cell death (Fang et al., Mol Vis, 2015. 21: p. 901-10) and T cell exhaustion (Jiang et al., Cell Death Dis, 2015. 6: p. e1792).

Continued treatment with PEG-rMuIL-10 as described in Example 3 changed the expression levels of PD1 on activated CD8+ T cell TILs. In mice, continued treatment with PEG-rMuIL-10 down regulated PD1 expression so as to maintain CD8+ T cells in a PD1+ mid-level expression state as compared to vehicle treated mice. The percentage of PD1+-high CD8+ T cell TILs in vehicle treated mice was 51.6%; PD1+-high CD8+ T cell TILs was only 9.78% in mice treated for 15 days with PEG-rMuIL-10. In contrast, the percentage of PD1+-mid CD8+ T cells was 17.9% in the vehicle treated mice, but increased to 31.2% in mice treated for 15 days with PEG-rMuIL-10.

Figure 3:
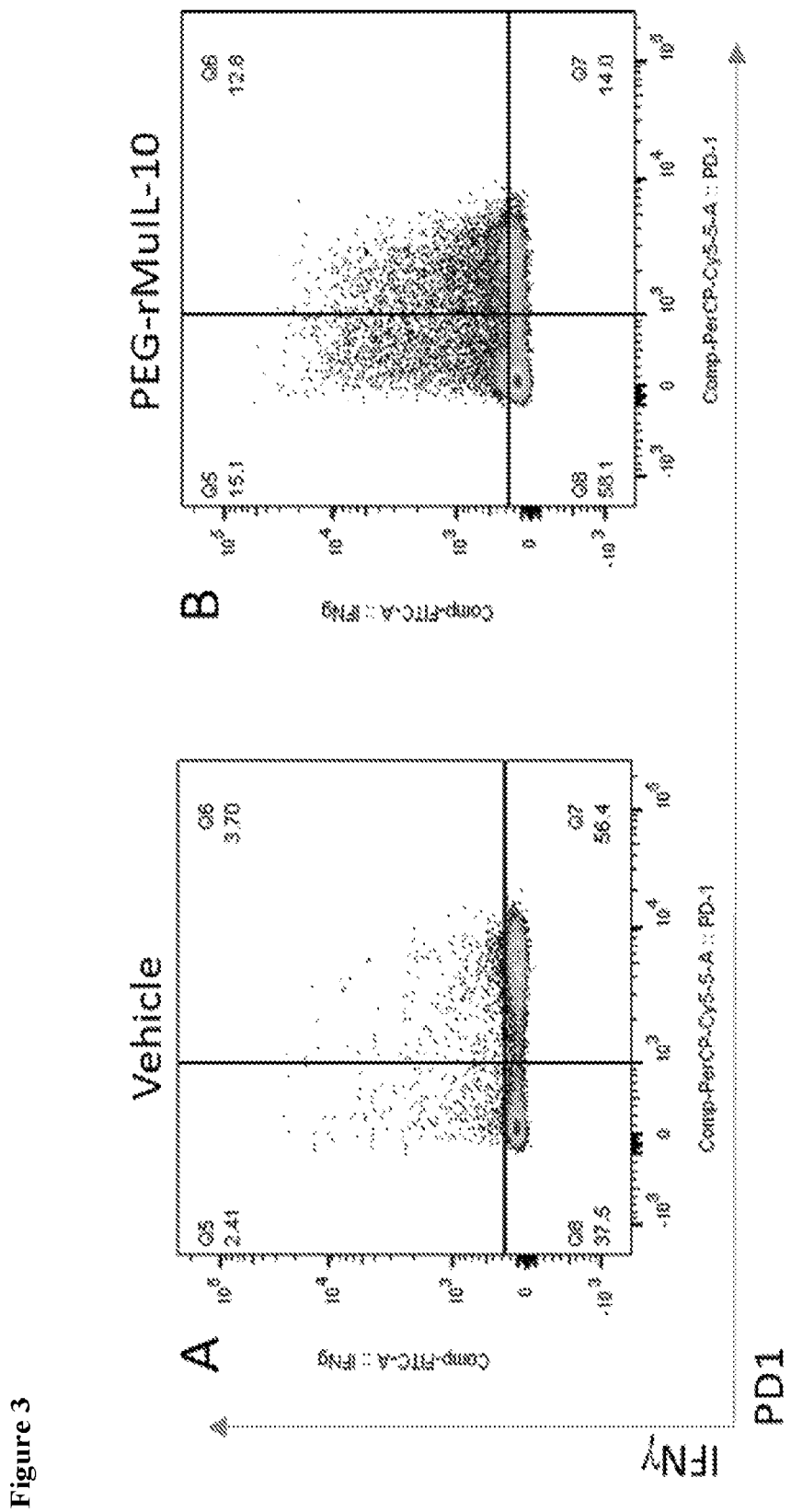
FIG. 3 illustrates the effects of prolonged IL-10 treatment (21-28 days) of tumor-bearing mice upon the ratio of IFNγ positive CD8+ T cell tumor infiltrating lymphocytes (TILs) that are PD1 positive.

In addition, prolonged treatment also changed the ratio of IFNγ positive CD8+ TILs that are PD1 positive. As illustrated above in FIG. 2, the IFNγ positive CD8+ TILs represent the tumor antigen specific CD8+ T cells within the tumor. These IFNγ positive, PD1 positive cells therefore represent the pool of tumor antigen specific CD8+ T cells. FIG. 3, Panel A shows that the pool of TILs from mice treated with vehicle and the amount of PD1+/−, CD8+ that are IFNγ positive. The PD1-, CD8+, IFNγ+ percentage in vehicle-treated mice is about 2.41%, while the PD1+, CD8+, IFNγ+ percentage in mice treated with PEG-rMuIL-10 for 15 days is about 3.7%. FIG. 3, Panel B shows that prolonged treatment with PEG-rMuIL-10 changes these percentages to 15.1% and 12.8%, respectively.

Thus, these data indicate that these IFNγ positive, PD1 positive cells represent the pool of tumor antigen specific CD8+ T cells from which antigen-specific TCR sequences (e.g., alpha and beta TCR sequences). can be obtained.

Example 5: PD1+CD8+ Peripheral T Cell Induced by IL-10 Therapy are CD45RO+ T Cells (Memory T Cells)

Figure 4:
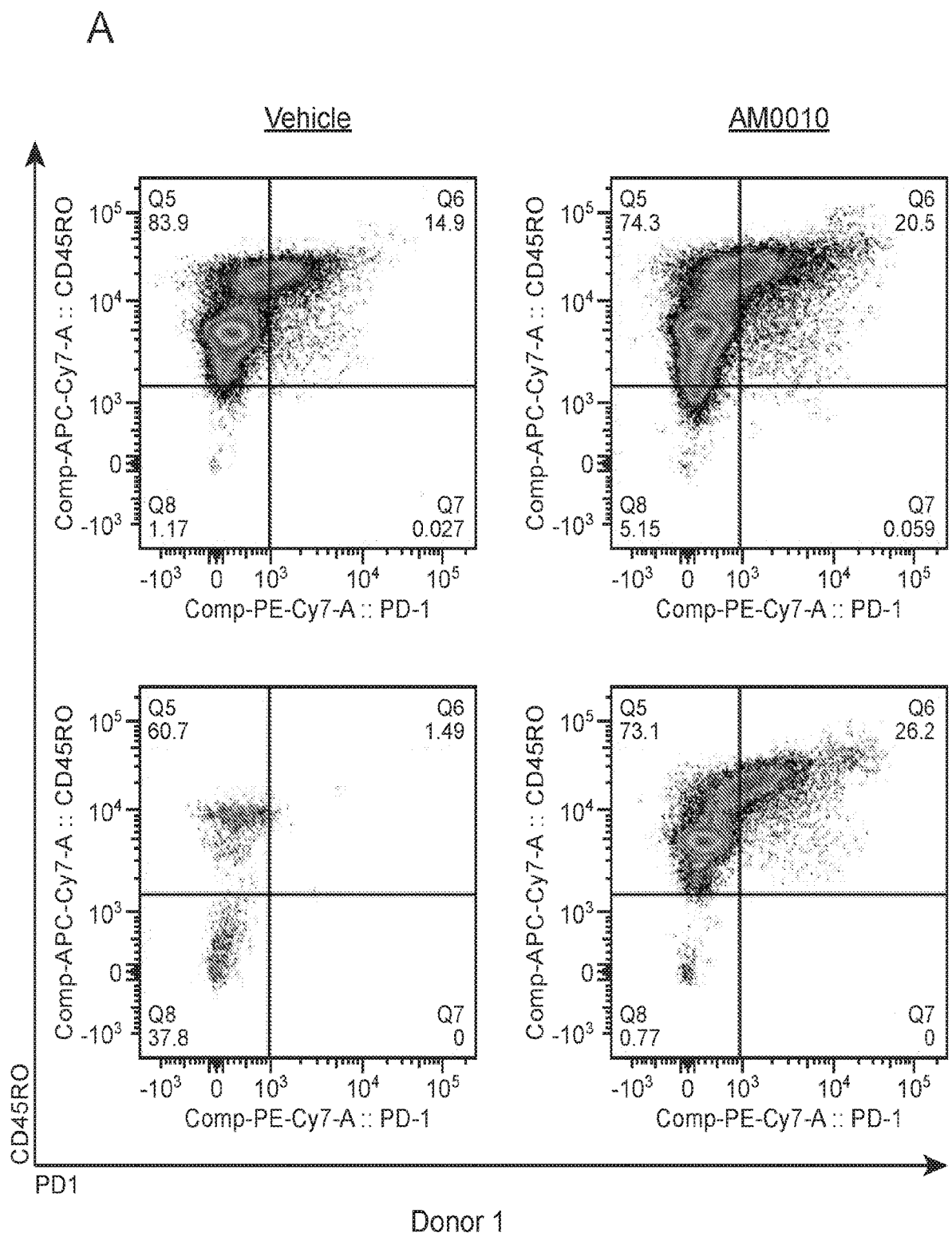
FIG. 4 illustrates the expression of CD45RO on PD1+ CD8+ T cells obtained from the periphery of a melanoma patient who exhibited a partial response to IL-10 monotherapy (Panel A) and on PD1+CD8+ T cells obtained from the periphery of a RCC patient who exhibited a partial response to IL-10 monotherapy (Panel B).
Figure 4:
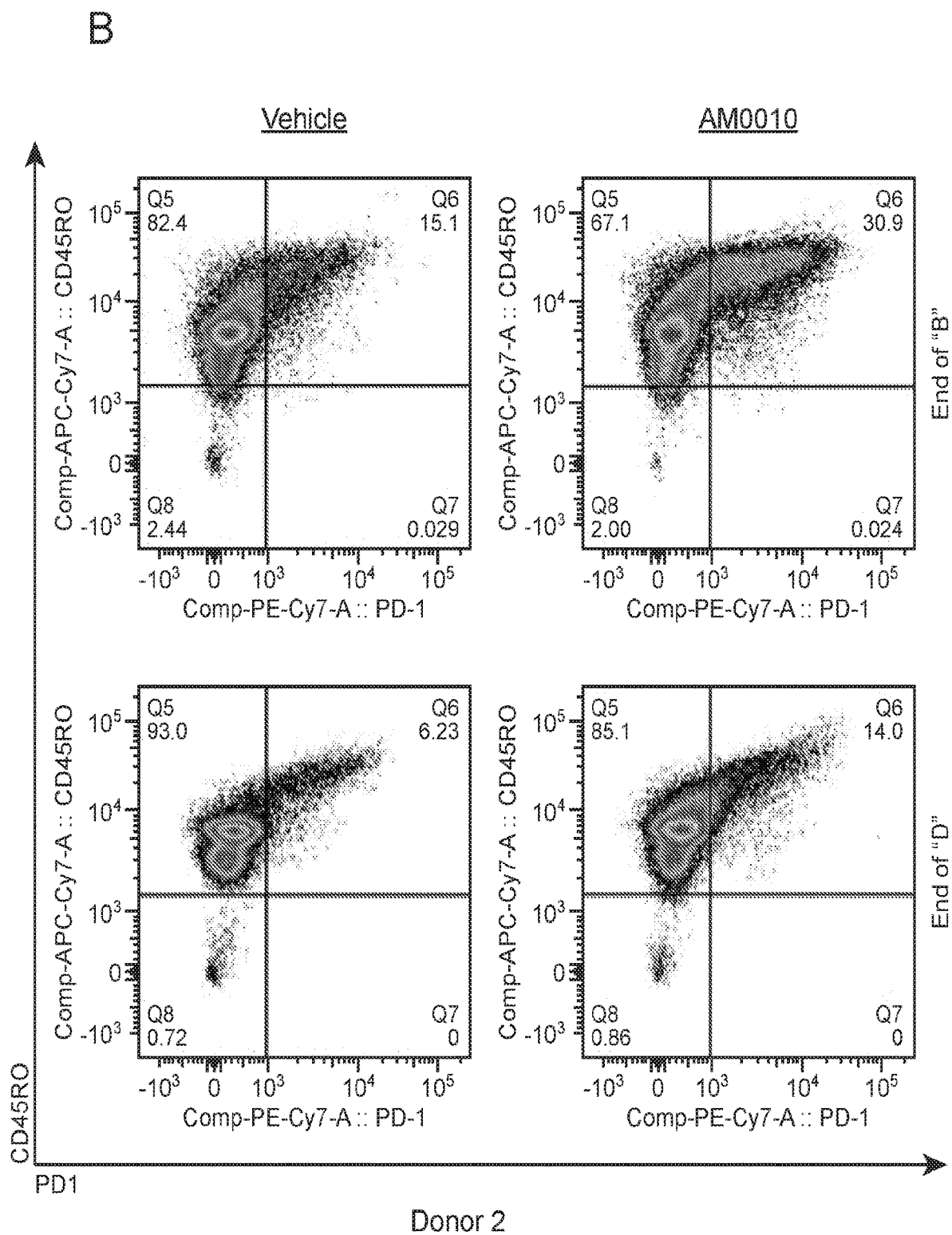

PD1+CD8+ peripheral T cells from normal healthy donors were analyzed further to assess their phenotype. A model of activation-induced cell death was used to assess these T cells in which peripheral CD8+ T cells are exposed to multi rounds of anti-CD3/anti-CD28 re-stimulation, and the activated cells exposed to PEG-rHuIL-10 (AM0010) or vehicle (control) during the rest phase. The cells were then analyzed for surface expression of both PD1 and CD45RO, a marker of T memory cells. As shown in FIG. 4, treatment of CD8+ T cell with IL-10 in this manner leads to the accumulation of PD1+ memory CD8+ T cells.

Panels A and B of FIG. 4 represent results using peripheral T cells obtained from two different donors. Panel A provides the results of analysis of peripheral CD8+ T cells from normal, healthy donors. CD8+ T cells were isolated, activated for 3 days and exposed to AM0010 for 3 days. After the 3 day rest period cells were analyzed by flow cytometry to determine their PD1 and CD45RO cell surface expression, (end of B). These cells were then restimulated for 3 days and then exposed to AM0010 for three days. After the 3 day rest period cells were analyzed by flow cytometry to determine their PD1 and CD45RO cell surface expression, (end of D). After multiple rounds of restimulation, the exposure of these cells to AM0010 results in more viable PD1+ cells, suggesting AM0010 prevents activated induced cell death. These cells are antigen specific by virtue of their memory phenotype (CD45RO+), and they are activated by virtue of their PD1 expression levels. The same cells are likely the IFNγ positive cells described by Chan et al (J Interferon Cytokine Res (2015) 35(12): 948-955) since the stimulatory conditions are similar.

These data indicate that the PD1+, CD8+ peripheral CD8+ T cells induced by IL-10 therapy represent activated, tumor antigen specific CD8+ T cells in these patients.

Example 6: Assessment of Peripheral T Cell Expansion in Il-10-Treated Patients

Figure 5:
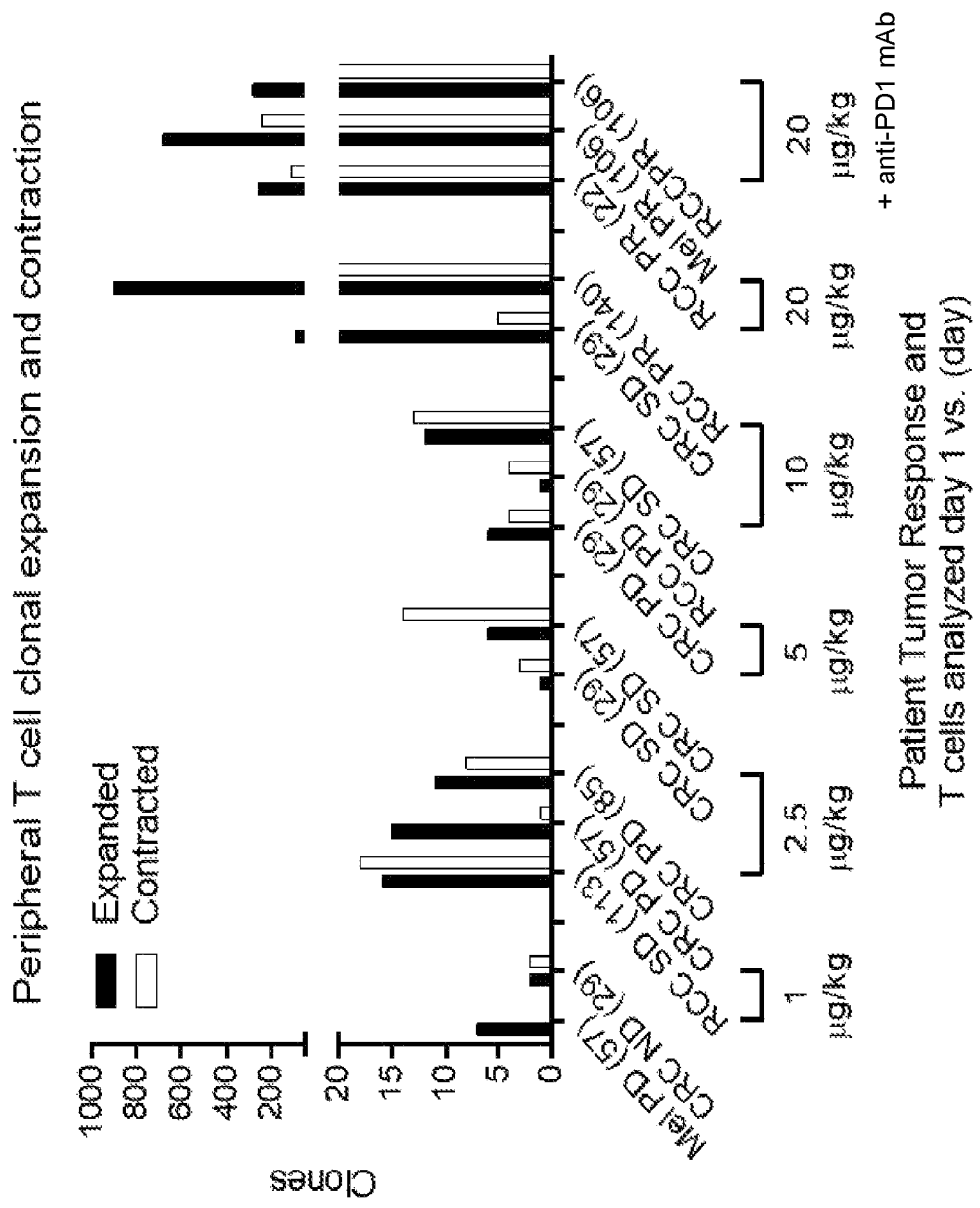
FIG. 5 shows patient tumor response and the relative numbers of expanded and contracted T cell clones in peripheral blood of cancer patients following administration of the indicated daily doses of AM0010. Patient tumor response was analyzed at the post-treatment day indicated in parentheses. The number of expanded and contracted T cell clones analyzed by comparing T cell clones present at the indicated posttreatment day as compared to prior to day 1 prior to administration of AM0010. Mel=melanoma; CRC=colorectal cancer; RCC=renal cell carcinoma; PD=progressive disease; SD=stable disease; PR=partial response; "anti-PD1 mAb"=anti-PD1 monoclonal antibody.

The effect of IL-10 treatment of patients on their peripheral PD1+CD8+ T cells was assessed (FIG. 5). PBMCs were obtained from cancer patients having melanoma (Mel), renal cell carcinoma (RCC), or colorectal cancer (CRC) and who had received PEG-IL-10 (AM0010) monotherapy as described above or PEG-IL-10 (AM0010) therapy in combination with an anti-PD1 monoclonal antibody. Peripheral blood samples obtained prior to initiation of PEG-IL-10 therapy served as a reference sample. Samples were obtained from patients on the day indicated in parentheses in FIG. 5; the dose of PEG-IL-10 (AM0010) administered is indicated on the X-axis of FIG. 5. Patients were classified as having progressive disease (PD), stable disease (SD), or at least a partial response (PR). Nucleic acids encoding at least the Vbeta TCR polypeptides were sequenced in the test sample and in the reference sample, and the frequency of nucleic acid encoding at least the Vbeta TCR polypeptide sequences in the test sample compared to the frequency of nucleic acid encoding the same Vbeta TCR in the reference sample. If the frequency increased in the test sample relative to the reference sample, the sequence was classified as being expressed by an "Expanded" T cell clone. If the frequency decreased in the test sample relative to the reference sample, the sequence was classified as being expressed by an "Contracted" T cell clone. "Expanded" clones represent disease antigen-specific T cells. The results are shown in FIG. 5.

Figure 6:
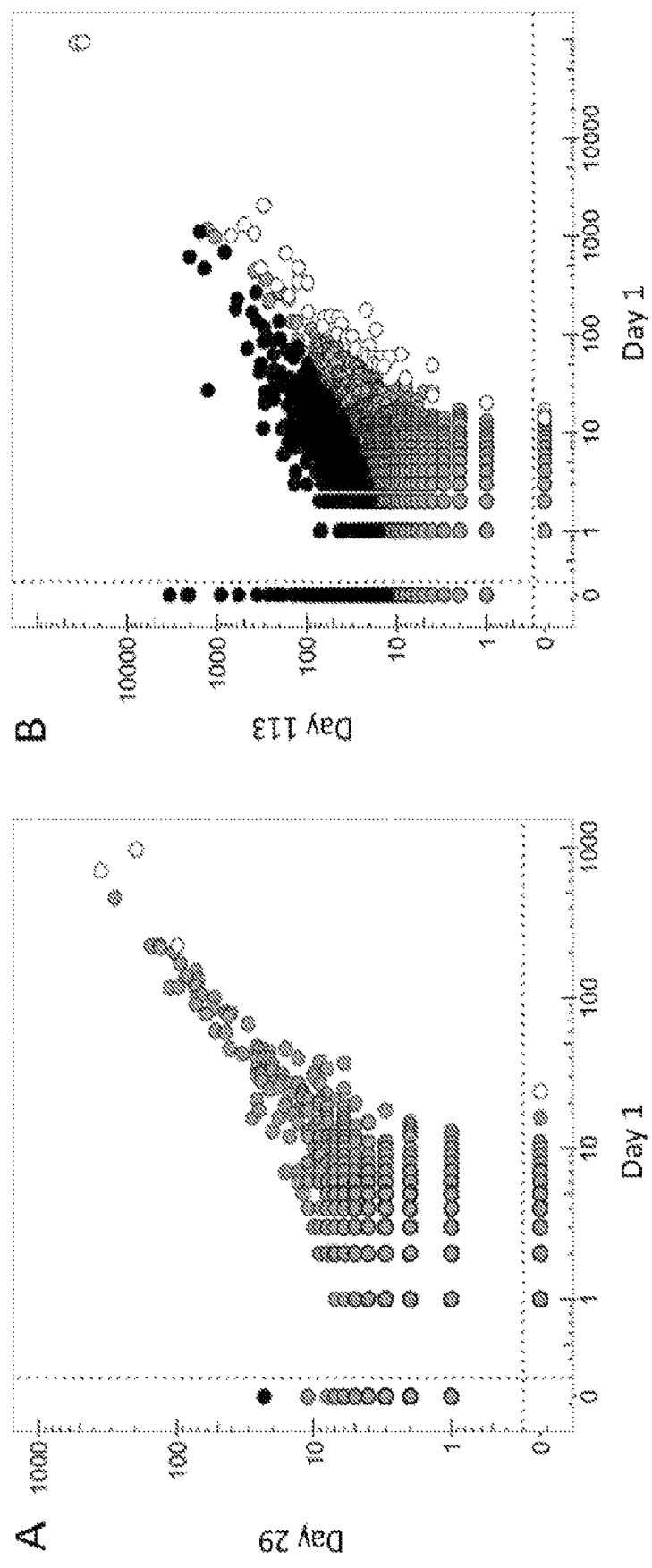
FIG. 6 shows the results of assessment of peripheral T cells in renal cell carcinoma patients who either exhibited progressive disease (Panel A) or exhibited an at least partial response (Panel B) following PEG-rHuIL-10 monotherapy.

Expansion of peripheral T cells was assessed in patients treated with PEG-rHuIL-10 (AM0010). FIG. 6 provides a representative analysis of expanding versus contracting peripheral T cell clones in two renal cell carcinoma patients treated with 10 µg/kg PEG-rHuIL-10 (AM0010), subcutaneous daily (Panel A) or 20 µg/kg PEG-rHuIL-10 (AM0010) subcutaneous daily (Panel B). The "Panel A" patient exhibited progressive disease (RCC PD), while the "Panel B" exhibited a 93% reduction in tumor mass, and thus exhibited an at least partial response (RCC PR). Peripheral T cells were obtained at both on day 1 prior to administration of first dose of PEG-rHuI:-10 and on day 29 of treatment. The black circles in FIG. 6 represent expanding clones from day 1 to the treatment day and the white circles represent contracting clones. The gray circles in FIG. 6 represent clones in the periphery that neither expanded nor contracted.

The RCC PD patient assessed in Panel A showed two expanding peripheral clones and four contracting clones after 29 days of treatment as compared to day 1. The RCC PR patient in Panel B shows 899 expanding clones versus 47 contracting clones after 113 days of treatment as compared to day 1.

These experimental data indicate that periphery of diseased patients who have an at least partial response to treatment with an IL-10 agent is a rich source of disease antigen-specific, PD1+, CD8+ T cells, which can be used to facilitate production of clonal populations of antigen-specific CD8+ T cells. Such clonal populations can be isolated, expanded in vitro, and used as a cell-based therapy (e.g., administered to a cancer patient having a disease of the same type (e.g., a tumor of the same type). The PD1+, CD8+ peripheral T cells can be obtained from the periphery of diseased patients who have an at least partial response to treatment with an IL-10 agent, the sequences of the T cell receptors (TCRs) obtained, and those sequences used to produce a library of alpha TCR and beta TCR sequences suitable for use in production of genetically modified T cells, e.g., T cells having a chimeric antigen receptor (CAR-T cells).

Example 7: Production of Library of TCR Alpha and/or Beta Sequences from PD1+, CD8+ T Cells Obtained from Periphery of Patients Responsive to Il-10 Agent Therapy As illustrated above, tissue samples (e.g., from peripheral blood) of patients who have a disease amenable to treatment with an IL-10 agent and have received IL-10 agent therapy, provide a source of antigen-specific CD8+ T cells. FIG. 7 provides an example schematic of how this source can be used to obtain sequences of the TCRs of such antigen-specific CD8+ T cells.

First, a source of CD8+ T cells is identified or obtained to serve as a patient test sample. This source can be, for example, a blood sample (or fraction of a blood sample) obtained from a patient. Such patients generally have any disease amenable to IL-10 therapy, which diseases include, but are not necessarily limited to, cancer (e.g., a solid tumor, such as melanoma, RCC, or lymphoma) and disease caused by infection by virus (e.g., HBV, HCV, HIV). The IL-10 agent treatment regimen will vary with a number of factors, such as the disease to be treated, the IL-10 agent to be administered (e.g., rHuIL-10, pegylated-rHuIL-10), and the like. The treatment regimen can be an IL-10 agent monotherapy or may be accompanied by other treatments for the condition (e.g., as in combination therapy). Patients who are at least partially responsive following treatment with an IL-10 agent monotherapy may be of particular interest.

Following any suitable processing of the patient test sample that may be desired, the nucleic acids encoding at least the Vbeta TCR polypeptide sequences present in the sample are obtained and sequenced. Optionally, the sample can processed to enrich for T cells prior to such nucleic acid processing and sequencing. For example, cells in the sample can be sorted by FACS to obtain a population of PD1+CD8+ T cells. Such cells may be optionally selected for PD1-mid expression level and/or may be optionally selected to be CD45RO+ and/or intracellular IFNγ+ and/or Granzyme B+ and/or Perforin+. Selection for intracellular IFNγ+ and/or Granzyme B+ and/or Perforin+ facilitates selection of activated, antigen specific cells. Where of interest, IFNγ can be induced prior to such selection via a 2-4 hour incubation with soluble anti-CD3 at 1-10 µg/ml. The PD1+, CD8+ T cells (or, e.g., PD1-mid, CD8+ T cells; CD45RO+PD1+, CD8+ T cells; CD45RO+, PD1-mid+, CD8+ T cells) can be optionally sorted to provide for single cell populations. The PD1+, CD8+ T cells can be optionally sorted based on their antigen specificity, using any suitable method (see, e.g., US 20060134704; US 20150275296), to provide for a population of T cells with a defined antigen specificity. Where of interest, the single or population of PD1+CD8+ T cells can then be optionally expanded in culture according to methods well known in the art.

The alpha and/or beta TCR genes can be isolated or sequenced using, for example, methodology provided by a commercial service such as Adaptive Biotechnologies or similar methodologies. (See, e.g., US 20140322716; US 20150275296; U.S. Pat. No. 9,043,160).

The TCR sequences obtained from the patient test sample are then be analyzed to determine the frequency of Vbeta and/or Valpha sequences present in the patient test sample as compared to the frequency of these same Vbeta and/or Valpha sequences in a reference sample. The reference sample can be a sample of the same tissue type from the patient prior to IL-10 agent therapy. Alternatively, or in addition, the reference sample can be a sample of the same tissue type from the same patient at a time point after initiation of therapy which is prior to the time point of the sample being analyzed. It is understood that the sequence data for such reference samples can be provided in a computer database, and sequence comparisons conducted in silico. Vbeta and/or Valpha TCR sequences that are increased in frequency in the patient test sample as compared of the reference sample represent the TCRs of clones that expanded in response to IL-10 agent therapy and/or continued IL-10 agent therapy.

The Vbeta and/or Valpha sequences can optionally be analyzed to identify any amino acid consensus sequences, and to identify amino acid consensus sequences in the context of both patient haplotype and type of disease (e.g., type of cancer). These alpha beta TCR genes represent endogenously generated, novel, disease antigen specific T cell receptor sequences that are specifically elicited by long term dosing with an IL-10 agent and which lead to potent anti-disease cell function.

TCR nucleic acids obtained can be used to generate a library containing multiple constructs (e.g., retroviral constructs) encoding the full alpha and/or beta TCR sequences. Such constructs are used to transduce pools of autologous patient peripheral CD8+ T cells with one or multiple TCR-encoding constructs so as to elicit monoclonal or polyclonal CD8+ T cell populations. Such monoclonal or polyclonal CD8+ T cell populations can be isolated, and reinfused back into the patient for treatment.

In some embodiments, a sample of diseased tissue containing patient CD8+ T cells (e.g., a solid tumor biopsy) is obtained from the patient prior to IL-10 agent treatment. This pretreatment sample can serve as an archival sample. This pretreatment sample is subjected to the same treatment as post-treatment samples as described above. Nucleic acid (e.g., DNA) is extracted and the TCR alpha and/or beta sequences in the pretreatment and posttreatment samples determined. Because Vβ TCR polypeptide sequences generally exhibit more variability between TCRs than Vα TCR polypeptides, sequence analysis at this stage can be performed on only the nucleic acids encoding Vβ TCR polypeptides. The TCR alpha and/or beta sequences can then be compared to determine which were present in T cells present in diseased tissue prior to IL-10 agent therapy, and of these sequences, which were increased in frequency following IL-10 agent therapy. The TCR sequences that increase in frequency following IL-10 agent therapy are identified as likely specific for an antigen of the diseased tissue (e.g., tumor antigen-specific), and represent TCRs present in T cell clones expanded by IL-10 agent therapy. Such TCR sequences are of particular interest for inclusion in the library of nucleic acids and/or clones.

Example 8. Treatment of Human Cancer Subjects with Peg-rhIL-10 Induces Proliferation of Cd8+ T Cell Clones that Correlate with Anti-Tumor Effect To evaluate the immune response in PEG-rhIL10 (AM0010)-treated patients and identify immune correlates to objective tumor responses, 83 immune-related cytokines, chemokines and serum proteins were repeatedly measured in 30 human subjects treated daily for 28 days with 20 µg/kg AM0010.

AM0010 induced an immune activation biased towards Th1 and Th2 regulation and CD8+ T cell activation. Th1 cytokines (IFNγ, IL-18, TNFα) as well as IL-3 and IL-4 which are products of activated Th2 CD4$^+$ and CD8$^+$ T cells were consistently increased. IL-7 was also significantly induced. AM0010 also increased cytotoxic effector molecules (FasL, lymphotoxin B) and decreased the immune suppressive cytokine TGFβ and the Th17-related cytokines which mediate chronic inflammation and tumor associated inflammation. IL-23, IL-17 and the homodimeric IL-12p40 were reduced by approximately 40% while IL-6 was not consistently altered. The increase in immune stimulating cytokines in the serum were sustained throughout the treatment duration and for periods up to at least 400 days. AM0010 induced the same consistent changes in IL-18 regardless of tumor type or radiographic tumor response.

Since the observed cytokine profile was indicative of activation of CD8$^+$ T cells in AM0010-treated patients, CD8$^+$ and CD4$^+$ T cells in the blood were analyzed. Immune checkpoints such as PD-1, Lag-3 or Tim-3 are inducible and expressed on T cells upon their activation. In addition, CD8$^+$ T cells having increased immune checkpoint expression represent a T cell repertoire that recognizes tumor antigens. Phenotypic changes in response to AM0010 treatment were evaluated with respect to checkpoint expression in T cells from the peripheral blood. AM0010 treatment increased Lag-3$^+$ CD8$^+$ T cells in the blood of a renal cell patient who had a durable tumor response. A significant proportion of the Lag-3$^+$ CD8$^+$ T cells were also, expressing PD-1. In all patients evaluated, the percentage of total PD-1+ T cells and of proliferating (KI-67+) PD-1+ CD8+ T cells increased throughout the treatment period, confirming the sustained immune activation suggested by the serum cytokines.

Increased activation of T cells leads to the upregulation of multiple checkpoints. The number of CD8+ T cells expressing Lag-3 and proliferating Lag-3+ CD8+ T cells was significantly and sustainably increased. However, Lag-3+ CD4+ T cells did not increase, indicating an immune activation focused on CD8+ T cell responses. Another immune checkpoint, Tim-3, induces T cell apoptosis and is associated with exhausted T cells in cancer patients. Tim-3 (or CTLA-4) was expressed only on a small proportion of CD8+ T cells and was not significantly upregulated. PD-1+ Lag-3+ double-positive CD8+ T cells and their proliferation increased continuously during AM0010 treatment indicating the sustained activation, rather than exhaustion, of those cells.

This activation profile correlated with clinical response. In an RCC patient with a delayed response, the proliferation of PD-1+ Lag-3+ CD8+ T cells coincided with the objective tumor response, suggesting their involvement in the response. Indeed, the prevalence of Lag-3+ PD-1+ CD8+ T cells and their proliferation in the patient after two months of treatment correlated with objective tumor response. In addition to leading to an increased prevalence of activated CD8+ T cells in the blood, AM0010 also increased the number of activated CD8+ T cells and the number of GranzymeB+ CD8+ T cells in the patients' tumor.

Example 9: Sequence Identification and Characterization of Expanding T-Cell Clones The increased proliferation and expansion of Lag-3+ PD-1+ CD8+ T cells in patients indicates the expansion of distinct, antigen challenged clonal T cell population and/or the functional maturation of an existing subset of peripheral T cells. To evaluate the contribution of each population, we analyzed the composition of the T cell repertoire of AM0010-treated patients by TCR-deep sequencing from the peripheral blood. DNA was isolated from EDTA blood samples using a DNeasy kit (Qiagen) and TCR deep sequencing was performed. Expanding and contracting clones were defined as T cell clones with more than 10-fold change between the pre-treatment and the on-treatment sample.

Comparison of the clonal T cell repertoire before and opon treatment revealed that patients on AM0010 had a strong expansion of T cell clones. Sequencing indicated the presence of 2,952 unique TCR CDR3 Vβ expanding sequences. The T cell expansion included clones which were detectable in the pre-treatment or pre-existing repertoire and clones which were not detectable in the patients before treatment (novel clones). The de-novo expansion was observed in patients with a wide variety of cancer types.

Clones which changed more than ten-fold from baseline were analyzed. AM0010 led to a more than ten-fold expansion of a median of 240 T cell clones per patient (range 17-786) while only a median of 18 T cell clones per patient (0-150) contracted more than 10-fold. On average, T cell clones which represented 0.06% of the T cell repertoire of the patients prior to treatment, expanded to 6% of the total peripheral T cell repertoire. The percentage of expanding T cells in the blood correlated with response. Patients who had an objective tumor response had a median of 15% expanding T cell clones (range 4.3-43%; >10-fold expansion/clone), compared to only 2.9% (0.99-4.3) in patients with stable disease and 1.8% (0.78-3.1) in patients who had progressive disease. Moreover, patients with an objective tumor response had a median of 761 (524-786) expanding individual clones, compared to 194 clones (81-519) in patients with stable disease and 164 clones (17-328) in patients with progressive disease.

Tumor responses to anti-PD-1 correlate with a high mutational burden in the tumor, suggesting that the pre-existing T cell response to the resulting neoantigens may facilitate the tumor response. A clonal expansion of rare or novel T cells was observed in all tumor types—with high or low predicted mutational burden and with high or low preexisting CD8+ T cells in the tumor tissue. While the magnitude of the de novo T cell expansion was correlated with tumor responses in patients on AM0010 monotherapy while autoimmune-related AEs were not observed. In prostate cancer patients receiving anti-CTLA-4 therapy, the expansion of more than 55 CD8+ T cell clones per patients preceded severe immune-related adverse events (irAEs), suggesting self-reactivity of these expanding T cell clones (Subudhi, S. K. et al. (2016) PNAS (USA) 113(42): 11919-11924).

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

That which is claimed is:

1. A method of treating a subject having a cancer that expresses a tumor antigen, which cancer is amenable to CD8+ T cell therapy and IL-10 therapy, the method comprising the following steps:
   (a) isolating CD8+ T cells from the subject and generating a reference T cell receptor (TCR) sample comprising a nucleic acid sequence encoding Vα TCR polypeptides and a nucleic acid sequence Vβ T cell receptor polypeptides from the isolated CD8+ T cells;
   (b) administering to the subject an IL-10 agent and subsequently isolating CD8+ T cells from the subject;
   (c) generating a test TCR sample comprising a nucleic acid sequence encoding the Vα TCR polypeptide and the nucleic acid sequence encoding a Vβ TCR polypeptide from the isolated CD8+ T cells of step (b);
   (d) administering to the subject a CD8+ T cell, wherein the T cell is genetically modified to express a recombinant TCR, the modified T cell comprising a sequence encoding the nucleic acid sequence encoding the Vα TCR polypeptide and the nucleic acid sequence encoding the Vβ TCR polypeptide of step (a) or (c)
   wherein, the sequence encoding the Vα TCR polypeptide and the sequences encoding the Vβ TCR polypeptide are increased in abundance in the test TCR sample as compared to the reference TCR sample; and
   wherein said administering is effective to treat the cancer in the subject.

2. The method of claim 1, wherein the Vα TCR polypeptide and the Vβ TCR polypeptide of the genetically modified T cell are encoded from separate expression cassettes of the same or different expression constructs.

3. The method of claim 1, wherein the Vα TCR polypeptide of the genetically modified T cell is encoded by the construct is operably linked at its C-terminus to a constant alpha TCR polypeptide.

4. The method of claim 1, wherein the Vβ TCR polypeptide of the genetically modified T cell is encoded by the construct is operably linked at is C-terminus to a beta constant TCR polypeptide.

5. The method of claim 1, wherein the Vβ TCR polypeptide and the Vα TCR polypeptide of the CD8+ T cell are encoded by a construct comprising a nucleic acid encoding a single chain TCR (scTv) comprising the Vβ TCR polypeptide and the Vα TCR polypeptide.

6. The method of claim 5, wherein the scTv comprises, from N-terminus to C-terminus, the Vβ TCR polypeptide, a linker, and the Vα TCR polypeptide.

7. The method of claim 1, wherein the cancer is a solid tumor.

8. The method of claim 7, wherein the tumor is a tumor of a cancer selected from cancer of the uterus, cervix, breast, prostate, testes, gastrointestinal tract, kidney, renal cell, bladder, bone, bone marrow, skin, head or neck, liver, gall bladder, heart, lung, pancreas, salivary gland, adrenal gland, thyroid, brain, ganglia, central nervous system (CNS) and peripheral nervous system (PNS), or cancer of the hematopoietic system, spleen, or thymus.

9. The method of claim 7, wherein the cancer is a cancer of the esophagus, oropharynx, stomach, small intestine, large intestine, colon, or rectum.

10. The method of claim 7, wherein the cancer is melanoma, colorectal cancer, or renal cancer.

11. The method of claim 1, wherein the method further comprises: step (c) administering to the subject an IL-10 agent after the subject is administered the genetically modified T cell of step (b).

12. The method of claim 1, wherein the Vα TCR polypeptide and the Vβ TCR polypeptide are increased in abundance by at least 10-fold in the test TCR sample as compared to the reference TCR sample.

13. The method of claim 1, wherein the subject is responsive to the IL-10 agent.

* * * * *

SEQUENCE LISTING

<160> NUMBER OF SEQ ID NOS: 36

<210> SEQ ID NO 1
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 1

Tyr Gly Arg Lys Lys Arg Arg Gln Arg Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 2

Arg Arg Gln Arg Arg Thr Ser Lys Leu Met Lys Arg
1               5                   10

<210> SEQ ID NO 3
<211> LENGTH: 27
<212> TYPE: PRT
<213> ORGANISM: Artificial Sequence
<220> FEATURE:
<223> OTHER INFORMATION: synthetic polypeptide

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 33
<212> TYPE: PRT
<213> ORGANISM: Artificial Sequence
<220> FEATURE:
<223> OTHER INFORMATION: synthetic polypeptide

<400> SEQUENCE: 4

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 5
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 6

Tyr Gly Arg Lys Lys Arg Arg Gln Arg Arg Arg
1               5                   10

<210> SEQ ID NO 7

```
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 7

Arg Lys Lys Arg Arg Gln Arg Arg Arg
1               5

<210> SEQ ID NO 8
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 8

Tyr Gly Arg Lys Lys Arg Arg Gln Arg Arg Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 9

Arg Lys Lys Arg Arg Gln Arg Arg
1               5

<210> SEQ ID NO 10
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 10

Tyr Ala Arg Ala Ala Ala Arg Gln Ala Arg Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 11

Thr His Arg Leu Pro Arg Arg Arg Arg Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 12

Gly Gly Arg Arg Ala Arg Arg Arg Arg Arg Arg
1               5                   10

<210> SEQ ID NO 13
<211> LENGTH: 5
```

```
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(5)
<223> OTHER INFORMATION: The sequence is repeated n times, where n is
      selected from an integer of at least 1 to 20.

<400> SEQUENCE: 13

Gly Ser Gly Gly Ser
1               5

<210> SEQ ID NO 14
<211> LENGTH: 3
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid is repeated m times, where m is
      selected from an integer of at least 1 to 20.
<220> FEATURE:
<221> NAME/KEY: MISC_FEATURE
<222> LOCATION: (1)..(3)
<223> OTHER INFORMATION: The sequence is repeated n times, where n is
      selected from an integer of at least 1 to 20.
<220> FEATURE:
<221> NAME/KEY: MISC_FEATURE
<222> LOCATION: (2)..(2)
<223> OTHER INFORMATION: The amino acid is repeated o times, where o is
      selected from an integer of at least 1 to 20.
<220> FEATURE:
<221> NAME/KEY: MISC_FEATURE
<222> LOCATION: (3)..(3)
<223> OTHER INFORMATION: The amino acid is repeated m times, where m is
      selected from an integer of at least 1 to 20.

<400> SEQUENCE: 14

Gly Ser Gly
1

<210> SEQ ID NO 15
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: The amino acid is repeated m times, where m is
      selected from an integer of at least 1 to 20.
<220> FEATURE:
<221> NAME/KEY: MISC_FEATURE
<222> LOCATION: (1)..(5)
<223> OTHER INFORMATION: The sequence is repeated n times, where n is
      selected from an integer of at least 1 to 20.
<220> FEATURE:
<221> NAME/KEY: MISC_FEATURE
<222> LOCATION: (2)..(2)
<223> OTHER INFORMATION: The amino acid is repeated o times, where o is
      selected from an integer of at least 1 to 20.
<220> FEATURE:
<221> NAME/KEY: MISC_FEATURE
<222> LOCATION: (3)..(3)
<223> OTHER INFORMATION: The amino acid is repeated m times, where m is
      selected from an integer of at least 1 to 20.
<220> FEATURE:
<221> NAME/KEY: MISC_FEATURE
<222> LOCATION: (4)..(4)
<223> OTHER INFORMATION: The amino acid is repeated o times, where o is
```

```
      selected from an integer of at least 1 to 20.
<220> FEATURE:
<221> NAME/KEY: MISC_FEATURE
<222> LOCATION: (5)..(5)
<223> OTHER INFORMATION: The amino acid is repeated m times, where m is
      selected from an integer of at least 1 to 20.

<400> SEQUENCE: 15

Gly Ser Gly Ser Gly
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(5)
<223> OTHER INFORMATION: The sequence is repeated n times, where n is
      selected from an integer of at least 1 to 20.
<220> FEATURE:
<221> NAME/KEY: MISC_FEATURE
<222> LOCATION: (5)..(5)
<223> OTHER INFORMATION: The amino acid is repeated m times, where m is
      selected from an integer of at least 1 to 20.

<400> SEQUENCE: 16

Gly Ser Gly Gly Ser
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(5)
<223> OTHER INFORMATION: The sequence is repeated n times, where n is
      selected from an integer of at least 1 to 20.
<220> FEATURE:
<221> NAME/KEY: MISC_FEATURE
<222> LOCATION: (4)..(4)
<223> OTHER INFORMATION: The amino acid is repeated m times, where m is
      selected from an integer of at least 1 to 20.

<400> SEQUENCE: 17

Gly Ser Gly Ser Gly
1               5

<210> SEQ ID NO 18
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(4)
<223> OTHER INFORMATION: The sequence is repeated n times, where n is
      selected from an integer of at least 1 to 20.
<220> FEATURE:
<221> NAME/KEY: MISC_FEATURE
<222> LOCATION: (4)..(4)
<223> OTHER INFORMATION: The amino acid is repeated m times, where m is
      selected from an integer of at least 1 to 20.

<400> SEQUENCE: 18

Gly Gly Gly Ser
```

```
<210> SEQ ID NO 19
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 19

Gly Gly Ser Gly
1

<210> SEQ ID NO 20
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 20

Gly Gly Ser Gly Gly
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 21

Gly Ser Gly Ser Gly
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 22

Gly Ser Gly Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 23

Gly Gly Gly Ser Gly
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 24

Gly Ser Ser Ser Gly
1               5
```

```
<210> SEQ ID NO 25
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(5)
<223> OTHER INFORMATION: The sequence is repeated n times, where n is
      selected from an integer of at least 1 to 50.

<400> SEQUENCE: 25

Gly Ser Gly Gly Ser
1               5

<210> SEQ ID NO 26
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(4)
<223> OTHER INFORMATION: The sequence is repeated n times, where n is
      selected from an integer of at least 1 to 50.

<400> SEQUENCE: 26

Gly Gly Gly Ser
1

<210> SEQ ID NO 27
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (1)..(5)
<223> OTHER INFORMATION: The sequence is repeated n times, where n is
      selected from an integer of at least 1 to 50.

<400> SEQUENCE: 27

Gly Gly Gly Gly Ser
1               5

<210> SEQ ID NO 28
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 28

Gly Gly Gly Gly Ser
1               5

<210> SEQ ID NO 29
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 29

Gly Gly Ser Gly
```

```
<210> SEQ ID NO 30
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 30

Gly Gly Ser Gly Gly
1               5

<210> SEQ ID NO 31
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 31

Gly Ser Gly Ser Gly
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 32

Gly Ser Gly Gly Gly
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 33

Gly Gly Gly Ser Gly
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 34

Gly Ser Ser Ser Gly
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 35

Ser Ile Ile Asn Phe Glu Lys Leu
1               5
```

```
<210> SEQ ID NO 36
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 36

Gly Gly Gly Ser
1
```